(12) United States Patent
Yeh et al.

(10) Patent No.: US 12,178,626 B2
(45) Date of Patent: Dec. 31, 2024

(54) ENCAPSULATED GAS OR PARTIAL VACUUM CT CONTRAST MATERIAL

(71) Applicants: THE REGENTS OF THE UNIVERSITY OF CALIFORNIA, Oakland, CA (US); THE UNITED STATES GOVERNMENT as represented by THE DEPARTMENT OF VETERANS AFFAIRS, Washington, DC (US)

(72) Inventors: Benjamin M. Yeh, Hillsborough, CA (US); Yanjun Fu, San Francisco, CA (US)

(73) Assignees: THE REGENTS OF THE UNIVERSITY OF CALIFORNIA, Oakland, CA (US); THE UNITED STATES GOVERNMENT as represented by THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 17/473,590

(22) Filed: Sep. 13, 2021

(65) Prior Publication Data
US 2022/0096030 A1 Mar. 31, 2022

Related U.S. Application Data

(63) Continuation of application No. 15/567,907, filed as application No. PCT/US2016/028503 on Apr. 20, 2016, now abandoned.

(60) Provisional application No. 62/149,815, filed on Apr. 20, 2015.

(51) Int. Cl.
| | |
|---|---|
| *A61K 9/14* | (2006.01) |
| *A61B 6/00* | (2006.01) |
| *A61B 6/03* | (2006.01) |
| *A61K 9/10* | (2006.01) |
| *A61K 49/04* | (2006.01) |
| *A61K 9/50* | (2006.01) |

(52) U.S. Cl.
CPC ............... *A61B 6/481* (2013.01); *A61B 6/03* (2013.01); *A61B 6/032* (2013.01); *A61B 6/482* (2013.01); *A61B 6/484* (2013.01); *A61K 9/10* (2013.01); *A61K 49/0419* (2013.01); *A61K 9/50* (2013.01)

(58) Field of Classification Search
None
See application file for complete search history.

(56) References Cited

U.S. PATENT DOCUMENTS

| | | | |
|---|---|---|---|
| 4,951,673 | A | 8/1990 | Long |
| 5,205,290 | A | 4/1993 | Unger |
| 6,117,414 | A | 9/2000 | Unger |
| 6,146,657 | A | 11/2000 | Unger et al. |
| 2001/0022963 | A1 | 9/2001 | Klaveness et al. |
| 2001/0024639 | A1 | 9/2001 | Unger |
| 2008/0107744 | A1 | 5/2008 | Chu |

(Continued)

FOREIGN PATENT DOCUMENTS

| | | |
|---|---|---|
| JP | H06-506254 T | 7/1994 |
| JP | H10-500691 T | 1/1998 |

(Continued)

OTHER PUBLICATIONS

European Patent Office—Decision to be Granted a Patent dated Jun. 4, 2021 in corresponding European Application No. 16783797.0 (2 pgs).
European Patent Office—Intention to Grant a Patent dated Jan. 13, 2021 in corresponding European Application No. 16783797.0 (76 pgs).
Mongan J et al., In vivo Differentiation of Complementary Contrast Media at Dual-Energy CT. Radiology. 2012;265(1): 267-272.
Spilde et al., "Evaluation of an Experimental Low-Attenuation Gastrointestinal Contrast Agent for CT Imaging of Intestinal Ischemia in an Animal Model". Acad. Radiol. 1999;6:94-101.

(Continued)

*Primary Examiner* — Jake M Vu
(74) *Attorney, Agent, or Firm* — Morgan, Lewis & Bockius LLP; Jeffry S. Mann

(57) ABSTRACT

The present invention provides an encapsulated gas or partial vacuum particle contrast media for use in CT imaging. In an exemplary embodiment, the invention provides an enteric contrast medium formulation. An exemplary formulation comprises, (a) an enteric contrast medium comprising a encapsulated gas or partial vacuum particle suspended in water. Exemplary encapsulated gas or partial vacuum particle has a specific gravity between 0.2 and 1.5. In various embodiments, the encapsulated gas or partial vacuum particle is suspended in aqueous media by an agent compatible with enteric administration of the formulation to a subject in need of such administration. In an exemplary embodiment, the contrast material is incorporated into a pharmaceutically acceptable carrier in which the material is suspended homogeneously. In an exemplary embodiment, the encapsulated gas or partial vacuum particle comprises 5% or more of the weight of the contrast material formulation. The invention also provides methods for imaging of the abdomen by dual energy CT or spectral CT contemporaneously with the delivery of the encapsulated gas or partial vacuum particle contrast material into the bowel lumen with or without the deliver of a second complementary contrast material into the blood vessels or other body compartments. The invention also provides methods for the digital separation of CT signal produced by the contrast media of the invention from the CT signal produced by other contrast media or bodily tissues to generate multiple resultant CT images with the contrast medium of the invention subtracted or highlighted.

12 Claims, 21 Drawing Sheets

(56) References Cited

U.S. PATENT DOCUMENTS

| | | | |
|---|---|---|---|
| 2009/0297441 A1* | 12/2009 | Canham | A61K 49/06 424/9.4 |
| 2013/0225455 A1 | 8/2013 | Amos et al. | |
| 2017/0050046 A1* | 2/2017 | Walder | A61N 5/062 |
| 2017/0354755 A1 | 12/2017 | Weinberger et al. | |

FOREIGN PATENT DOCUMENTS

| | | |
|---|---|---|
| JP | H10-500692 T | 1/1998 |
| JP | 2018-513837 | 5/2018 |
| WO | WO 1992/017514 | 10/1992 |
| WO | WO 1995/032005 | 11/1995 |
| WO | WO 1995/032006 | 11/1995 |
| WO | WO 1998/043558 | 10/1998 |
| WO | WO 2011/149985 | 12/2011 |
| WO | WO 2015/024025 | 2/2015 |
| WO | WO 2016/172256 | 10/2016 |

OTHER PUBLICATIONS

Yu S, Watson A. Metal-Based X-ray Contrast Media. Chem Rev. 1999; 99(9):2353-2378.

3M (https://multimedia.3m.com/mws/media/4915510/3mtm-im30k-hi-strength-glass-bubbles-tech-info.pdf (downloaded on Jun. 7, 2020) (2020).

Liberman et al (Hollow silica and silica-boron nano/microparticles for contrast-enhanced ultrasound to detect small tumors. Biomaterials 33 (2012).

Tang et al (Nonporous Silica Nanoparticles for Nanomedicine Application. Nano Today. 8(3): 290-312) (2013).

JP 2017-545630 Application—Office Action dated Dec. 24, 2019.

Zerda et al. "Proceedings of the 2009 World Molecular Imaging Congress Montreal, Canada, Sep. 23-26", Molecular Imaging and Biology, Springer-Verlag, NE, vol. 12, No. 1, Nov. 3, 2009 (2009), pp. 2-461.

European Patent Office—Extended Search Report for corresponding EP Divisional Application No. 21182614.4 dated Jan. 28, 2022.

* cited by examiner

FIG. 7

|  | CT Number (Hounsfield Units) | | | | | | Change in CT number from 40 to 140 keV (HU) |
|---|---|---|---|---|---|---|---|
|  | kVp setting | | keV reconstruction | | | | |
|  | 80 | 140 | 40 | 60 | 70 | 140 | |
| Water | 3.1 | 0.9 | 3.87 | -5.32 | -7.41 | -10.13 | 14 |
| 0.1% iodine in water | 53 | 25 | 97 | 36 | 21 | -5.7 | 103 |
| 0.1% barium in water | 54 | 20 | 103 | 40 | 25 | -3.0 | 106 |
| Borosilicate hollow microsphere 30% w/w in water | -39.1 | -118.2 | 132 | -73 | -122 | -214 | 346 |
| 0.1% iodine with borosilicate hollow microsphere 30% w/w in water | 14.7 | -82 | 225 | -32 | -93 | -210 | 435 |
| 0.1% barium with borosilicate hollow microsphere 30% w/w in water | 5.5 | -93.1 | 215 | -40 | -100 | -214 | 429 |

FIG. 10

| Substance | 80 kVp (HU) | 140 kVp (HU) | 80:140 kVp HU ratio |
|---|---|---|---|
| Low x-ray attenuation materials (hydrocarbons) | | | |
| Canola olive oil 100% | -140 | -109 | 1.28 |
| Paraffin | -147 | -106 | 1.39 |
| Human / animal subcutaneous fat | -110 | -89 | 1.23 |
| High x-ray attenuation materials (Radiodense materials in water) | | | |
| Iohexol (5mg I/mL) in water | 210 | 121 | 1.74 |
| Iohexol (15mg I/mL) in water | 625 | 347 | 1.80 |
| Iohexol (35mg I/mL) in water | 1409 | 785 | 1.79 |
| 5% lipiodol emulsion in 2.5% triton 100 in water | 738 | 419 | 1.76 |
| Colloid $SiO_2$ 50% (Ludox commercial product) | 572.4 | 452.2 | 1.27 |
| 50% Crystal $SiO_2$ (1-5μm) in H2O, no additives, | 635.5 | 501.6 | 1.22 |
| 60% crystal $SiO_2$ (1-5μm) in H2O, no additives, | 834.7 | 662.9 | 1.21 |
| Hydrocarbons with iodinated radiodense material | | | |
| 3.33% lipiodol in canola olive oil | 596 | 309 | 1.93 |
| 2% lipiodol in canola olive oil | 169 | 69 | 2.45 |
| 0.7% lipiodol in canola olive oil | 73.4 | 12.9 | 5.69 |
| Hydrocarbon bonded with silicon radiodense material | | | |
| Silicone Oil 100% 50 cSt (Fisher Scientific) | 212 | 82 | 2.58 |
| Silicone oil 100% 350 cSt (Sigma Aldrich) | 209 | 84.2 | 2.48 |
| Silicone oil 50 cSt 75% emulsion in H2O (Sigma Aldrich) | 164 | 61.2 | 2.67 |
| Silicone oil 350 cSt 75% emulsion in H2O (Sigma Aldrich) | 167 | 66.6 | 2.52 |

FIG. 11

| Substance | 80 kVp (HU) | 140 kVp (HU) | 80:140 kVp HU ratio |
|---|---|---|---|
| Low x-ray attenuation material | | | |
| Room air / vacuum | -1000 | -1000 | 1 |
| | | | |
| High x-ray attenuation materials | | | |
| Silicone rubber without bubbles (Smoothon Moldstar 15) | 453 | 274 | 1.65 |
| Solid borosilicate glass | 1242 | 1031 | 1.21 |
| Solid silica glass | 1332 | 1040 | 1.28 |
| Iohexol (5mg I/mL) in water | 210 | 121 | 1.74 |
| Barium sulfate 2.0% w/w in water | 578 | 334 | 1.73 |
| Plaster of paris 40% w/w in water | 998 | 690 | 1.45 |
| | | | |
| Gas or partial vacuum combined with high-attenuating materials | | | |
| | | | |
| Silicone rubber (Smoothon Moldstar 15) with small to moderate quantity of room air bubbles | 222 | 65 | 3.41 |
| Silicone rubber (Smoothon Moldstar 15) with moderate quantity of room air bubbles | 176 | 37 | 4.75 |
| Silicone rubber with 38% w/w iM30K | 185 | 4 | 46.3 |
| Silicone rubber with 40% w/w iM30K | 167 | -11 | -15.2 |
| Hollow borosilicate microspheres 40% w/w in water (iM30K from 3M, spec gravity 0.6, ~15 micron diameter) | -45 | -137 | 0.33 |
| Hollow borosilicate microspheres 40% w/w in water (S60HS from 3M, spec gravity 0.6, ~30 micron diameter) | -27.5 | -120 | 0.23 |
| Hollow borosilicate microspheres 30% w/w in water (S60HS from 3M, spec gravity 0.6, ~30 micron diameter) | -17.1 | -90.7 | 0.19 |
| Iohexol (8.75mg I/mL) + 30% w/w iM30K | 321 | 81 | 3.96 |
| Barium sulfate 1.67% with 12% iM30K w/w in water | 483 | 246 | 1.96 |
| Barium sulfate 1.47% with 17.5% iM30K w/w in water | 397 | 178 | 2.23 |
| Barium sulfate 1.37% with 20.5% iM30K w/w in water | 374 | 155 | 2.41 |
| Barium sulfate 1.28% with 23% iM30K w/w in water | 346 | 126 | 2.75 |
| Barium sulfate 1.0% with 30% iM30K w/w in water | 264 | 42 | 6.29 |
| Plaster of paris, 40% w/w in water, set, then dessicated (water replaced with gas) | 203 | -78 | -2.60 |

FIG. 12

| Substance | CT number (HU) at virtual monoenergetic 40 keV reconstruction | CT number (HU) at virtual monoenergetic 140 keV reconstruction |
|---|---|---|
| Low x-ray attenuating material | | |
| Room air / vacuum | -1000 | -1000 |
| | | |
| High x-ray attenuating material | | |
| Solid Borosilicate glass | 749 | 253 |
| Amorphous Silica | 851 | 290 |
| Silicone rubber without bubbles (Smoothon Moldstar 15) | 904 | 64 |
| Iohexol (5mg I/mL) in water | 430 | 4.2 |
| Barium sulfate 2.1% w/w in water | 1098 | 69.0 |
| | | |
| Encapsulated gas or partial vacuum particle with high x-ray attenuating material shells | | |
| Hollow borosilicate microspheres 30% w/w in water (iM30K from 3M, spec gravity 0.6, ~15 micron diameter) | 919 | -170 |
| Hollow borosilicate microspheres 40% w/w in water (S60HS from 3M, spec gravity 0.6, ~30 micron diameter) | 173 | -289 |
| Silicone rubber (Smoothon Moldstar 15) with small to moderate quantity of room air bubbles | 650 | -64 |
| Silicone rubber (Smoothon Moldstar 15) with moderate quantity of room air bubbles | 550 | -104 |
| Silicone rubber with 40% w/w iM30K | 594 | -227 |
| Iohexol (8.75mgI/mL) + 30% w/w iM30K | 796 | -238 |
| Barium sulfate 1.67% with 12% iM30K w/w in water | 983 | -42.4 |
| Barium Sulfate 1.47% with 17.5% iM30K w/w in water | 917 | -95.6 |
| Barium sulfate 1.37% with 20.5% iM30K w/w in water | 881 | -124 |
| Barium sulfate 1.28% with 23% iM30K w/w in water | 828 | -148 |
| Barium sulfate 1.0% with 30% iM30K w/w in water | 777 | -196 |

FIG. 13

| | CT Number (Hounsfield Units) | | | | | | 80:140 kVp CT Number Ratio |
|---|---|---|---|---|---|---|---|
| | keV reconstrucion | | CT kVp setting | | | | |
| | 40 | 140 | 80 | 100 | 120 | 140 | |
| *High x-ray attenuation materials* | | | | | | | |
| Conventional contrast agents | | | | | | | |
| Iohexol 15 mg/mL | 1249 | 13.8 | 655 | 525 | 435 | 368 | 1.78 |
| Readi-Cat Ba 2%w/w | 1064 | 57 | 545 | 445 | 374 | 323 | 1.69 |
| $BaSO_4$ 20mg/mL | 990 | 57 | 513 | 410 | 355 | 300 | 1.71 |
| Silicon-containing materials | | | | | | | |
| Fused silica 50% wt in $H_2O$ | 901 | 276 | 600 | 547 | 506 | 470 | 1.28 |
| Crystaline silica 50% wt in $H_2O$ | 992 | 340 | 666 | 596 | 547 | 520 | 1.28 |
| *Encapsulated gas or partial vacuum particle formulations* | | | | | | | |
| Silicon-containing materials | | | | | | | |
| Borosilicate hollow microsphere 40% iM30K in $H_2O$ | 171 | -257 | -45 | -89.7 | -119 | -137 | 0.33 |
| Borosilicate hollow microsphere 40% S60HS in $H_2O$ | 165 | -278 | -52 | -104 | -132 | -154 | 0.34 |
| Further additions of conventional contrast to borosilicate hollow microspheres | | | | | | | |
| Iohexol 8.75mg I /mL + 30.3% iM30K in $H_2O$ | 919 | -170 | 376 | 255 | 186 | 134 | 2.82 |
| Barium Readi-Cat 1% and 29.5% iM30K | 742 | -194 | 268 | 169 | 101 | 59 | 4.54 |

FIG. 14

|  | Iodine / barium | VoLumen / water or other neutral oral contrast | Hydrocarbon oil based agents | Heavy metal agents (e.g. W, Ta, Au, Yb agents) | Encapsulated gas or vacuum contrast material |
|---|---|---|---|---|---|
| Visibly different than IV contrast agents and bone at CT |  | ✓ | ✓ |  | ✓ |
| Visibly different than tumors, abscesses, fluid, and normal tissues at CT | ✓ |  | ✓ | ✓ | ✓ |
| Provides positive, neutral, and negative signal at dual energy or spectral CT |  |  |  |  | ✓ |
| Visibly different than fat at dual energy or spectral CT | ✓ | ✓ |  | ✓ | ✓ |
| Lowers radiation dose with automated exposure control |  | ✓ | ✓ |  | ✓ |

FIG. 15

| Material | CT scanner manufacturer | CT number | | | | 80:140 kVp CT number ratio |
|---|---|---|---|---|---|---|
| | | 80 kVp | 100 kVp | 120 kVp | 140 kVp | |
| Iohexol 8.75 mg I/mL | GE | 376 | 300 | 249 | 212 | 1.77 |
| | Siemens | 364 | 279 | 230 | 198 | 1.84 |
| Readicat | GE | 572 | 459 | 382 | 328 | 1.74 |
| | Siemens | 570 | 451 | 376 | 326 | 1.75 |
| 30% wt/wt 17 um diameter borosilicate glass hollow microspheres in water | GE | -7 | -46 | -70 | -87 | 0.08 |
| | Siemens | -9 | -52 | -69 | -87 | 0.10 |
| 20% wt/wt 17 um diameter borosilicate glass hollow microspheres in water with 10 mg/mL iohexol | GE | 435 | 301 | 216 | 160 | 2.72 |
| | Siemens | 413 | 275 | 195 | 147 | 2.81 |
| 20% wt/wt 17 um diameter borosilicate glass hollow microspheres in water with 2% wt barium sulfate | GE | 492 | 348 | 254 | 189 | 2.60 |
| | Siemens | 470 | 320 | 231 | 171 | 2.75 |

FIG. 17

| Hollow microsphere shell composition | Brand name (company) and average diameter | Specific gravity (g/cc) | 80 kVp CT number (HU) | 140 kVp CT number (HU) | 80:140 kVp CT number ratio |
|---|---|---|---|---|---|
| Borosilicate glass | Im30K (3M) 18 micron | 0.6 | -23 | -105 | 0.22 |
| Borosilicate glass | 45P25 (Potters) 23 micron | 0.45 | -163 | -196 | 0.83 |
| Borosilicate glass | C-PHGL-18 (Corpuscular) 18 micron | 0.6 | 5 | -80 | -0.06 |
| Barium doped borosilicate glass | Custom made | 0.55 | -74 | -179 | 0.41 |
| Zinc oxide glass about 20% ZnO w/w coating | HGMS-ZnO (Cospheric) 1-30 micron | 0.66 | 399 | 135 | 2.95 |
| Titanium dioxide glass. (coated with rutile $TiO_2$) | Isospheres (Cospheric) 5-30 micron | 0.59 | -63 | -137 | 0.46 |
| Nickle-plated glass | HGMS-Ni (Cospheric) 5-30 micron | 0.7 | 147 | -5 | -29 |
| Nickle metal coated glass | M-18-Ni (Cospheric) 5-30 micron | 0.69 | 309 | 99 | 3.12 |
| Silver metal coated glass | M-18-Ag (Cospheric) 5-30 micron | 0.72 | 2186 | 1116 | 1.96 |
| Phenolic (Benzene, ethenyl-, homopolymer; phenol formaldehyde resin) | Phenolic (Polysciences) 5-127 micron | 0.2-0.8 | -452 | -449 | 1.01 |
| Ceramic ($SiO_2$ 56-58%; $Al_2O_3$ 34-37%; $Fe_2O_3$ < 2%; $TiO_2$ < 1.5%) | W100 TUF (Intercorp) 50-80 micron | 0.8 | 13 | -63 | -0.21 |
| Ceramic ($SiO_2$ 54%; Al2O3 41%; $Fe_2O_3$ 1.8%; CaO 1.1%; $TiO_2$ 0.23%) | QK100 (Sun Microsphere) < 100 micron | 0.8 | 72 | -10 | -7 |
| | QK300 (Sun Microsphere) < 300 micron | 0.92 | 70 | -6 | -12.3 |
| 20% w/w silver-coated ceramic (40-70% glass oxide, 15-50% silver, 10-17% mullite, 0.1-0.8% crystalline silica) | AG-SF-20 Conduct-o-fil (Potters) 50 micron | 0.82 | 1601 | 810 | 1.98 |
| 32% w/w Silver coated ceramic (40-70% glass oxide, 15-50% silver, 10-17% mullite, 0.1-0.8% crystalline silica) | AG-SL150-30-TRD Conduct-o-fil (Potters) 82 micron | 1.11 | 2453 | 1292 | 1.90 |

ENCAPSULATED GAS OR PARTIAL VACUUM CT CONTRAST MATERIAL

CROSS-REFERENCE TO RELATED APPLICATIONS

This application is a Continuation of U.S. application Ser. No. 15/567,907 filed Oct. 19, 2017, which is a U.S. National Phase Application under 35 U.S.C. § 371 of International Application PCT/US16/28503, filed Apr. 20, 2016, which claims the benefit under 35 U.S.C. § 119 (e) of U.S. Provisional Application No. 62/149,815 filed on Apr. 20, 2015, both of which are incorporated by reference herein in their entireties.

SPONSORED RESEARCH OR DEVELOPMENT

This invention was made with government support under Grant Nos. EB013816 and TR000004 awarded by the National Institutes of Health. The government has certain rights in the invention.

BACKGROUND OF THE INVENTION

The use of contrast material for medical CT imaging is essential for many clinical scenarios, particularly in the abdomen and pelvis where numerous visceral organs and blood vessels show intertwined anatomy. Enteric contrast may be given into the bowel by mouth or through a tube and distend the bowel to improve its visualization.

Contrast material for the bowel may be "positive" and give signal that is substantially greater than water (e.g. >60 Hounsfield Units, or HU). These agents utilize materials with high X-ray attenuation properties. Alternatively, contrast material for the bowel may be "neutral" and give signal that resembles that of water or soft tissue (e.g. CT numbers between −20 and 60 HU). Contrast material for the bowel may also be "negative" and give signal that is lower than that of water (e.g. CT numbers below −20 HU), and these agents use materials with low X-ray attenuation properties.

All commercial positive CT contrast materials are based on iodine or barium. The difference in x-ray attenuation between positive agents and the soft tissues of the body are nearly or wholly due to the iodine or barium since the other atoms in these agents resemble those of bodily soft tissue and water.

The high value of positive enteric CT contrast, which marks bowel lumen with bright signal at CT imaging, is undisputed for the detection of extra-enteric fluid collections and masses which may resemble unopacified bowel at CT interpretation in a wide range of disease.

Despite the value of positive enteric contrast, bright enteric contrast material paradoxically obscures intravenous contrast CT findings for some of the most devastating of diseases, including 1) Trauma where contrast material leakage may be ambiguous for being from vascular bleeding versus bowel lumen origin; 2) Bowel ischemia and infarction where bowel wall non-enhancement may be obscured by bright intralumenal enteric contrast material; 3) Bowel inflammation where bowel wall hyper-enhancement by IV contrast is the most reliable feature of active disease; 4) enteric bleeding where iodinated contrast extravasation into bowel or enhancing tumors is masked by the presence of enteric contrast; and 5) three-dimensional image reformations of blood vessels.

Another problem with currently available positive clinical contrast materials is that they cannot be distinguished from each other or from other radiodense structures such as shrapnel, calcifications, surgical staple lines or implants at CT imaging. Even with Dual Energy CT (DECT) or multi-energy or spectral CT, now an increasingly widespread clinical technology that allows material decomposition of imaged voxels based on known 80:140 kVp CT number ratios of individual substances, iodine and barium-based contrast materials are not easily differentiated from each other because their 80:140 kVp CT number ratios are virtually identical. This limitation causes clinical errors and delays. For example, a CT scan enhanced with positive bowel barium and intravenous iodine contrast that shows contrast leakage into the peritoneum may be ambiguous for whether the leak is due to bleeding (iodine), bowel perforation (barium), or urinary tract injury (excreted iodine), each of which is a clinical emergency but requires dramatically different management. To resolve such ambiguity, scans may need to be repeated at the expense of lost time and therapeutic opportunity. Repeat CT scans also result in additional radiation dose. Increased public concern about CT radiation dose resulted in a 2011 NIH summit focused on CT dose reduction. CT scanners capable of multi-energy or spectral imaging are under development, but even with improved capability, these new CT technologies are unlikely to be able to readily differentiate iodinated from barium based contrast material.

Further limitations of current positive enteric CT contrast material are toxicity and complications. Barium-based agents may cause severe, potentially fatal peritonitis or aggravate infections at sites of leak, and may convert a partial bowel obstruction into a complete bowel obstruction. Iodinated agents may cause severe, even fatal pneumonitis when inadvertently aspirated and may also cause life threatening allergic-type reactions, and this concern limits its use in the up to 1% of patients with known prior reactions. This is likely related in part to the hyperosmolality of these agents. Moreover, several of these agents are brownish in color and poor-tasting. Some patients (up to 1-3%) have reactions to iodinated contrast material.

"Neutral" enteric CT contrast materials are valuable for CT imaging. Examples of neutral enteric contrast materials are water, milk, or a fluid with non-absorbable carbohydrates such as sorbitol or methylcellulose without or with only a minimal amount of iodine or barium (e.g. VoLumen®). Neutral enteric CT contrast agents are commonly used to expand the lumen of the bowel and allow intravenous contrast material to vividly show the relative hyper or hypo vascularity of the bowel wall which might otherwise be obscured by positive enteric contrast material. Since the signals from neutral agents resemble those of natural soft tissue or water, they may not allow as confident of a diagnosis as positive enteric contrast agents for bowel leak, extralumenal fluid collections, intraabdominal abscess, or hematoma.

"Negative" enteric contrast agents are not commonly used but have a CT number value less than −20 HU. Examples of these low x-ray attenuation contrast materials are hydrocarbon oils, such as peanut oil or vegetable oil, perfluorocarbons, and gas such as insufflated air or carbon dioxide, or chemically created carbon dioxide. Negative enteric contrast agents can provide excellent delineation of the bowel wall and bowel wall enhancement when given with intravenous contrast agents. The most commonly used negative enteric agents are carbon dioxide for gastric or colonic distension. However, the available negative agents have not been well tolerated for small bowel use. Although negative enteric contrast materials may resemble naturally occurring fat at CT, the detection of disease at CT rarely depends on the identification of an unusual amount of fat in the bowel. Gaseous enteric contrast agents, where gas is insufflated into or created in the bowel lumen, may not be as useful as positive enteric contrast materials to delineate bowel leakage. Even with dual energy CT, the signal of available negative agents cannot be distinguished from that of naturally-occurring fat or abnormal gas collections. Practical non-expansile non-oil-based negative contrast agents that can be delivered in liquid form are not currently available.

A further limitation of enteric insufflated gas or gas-forming agents as contrast agents is that enteric gas causes more motion artifact at CT than does enteric fluid (FIGS. 2 and 19).

Encapsulated gas contrast material has been previously described for ultrasound and MRI (usually perfluorocarbon). Encapsulated gas contrast material was also explored for CT (e.g. MRX80, which is based on perfluorocarbon). Partial vacuum agents have not been explored for CT as a contrast material.

Modern dual energy and spectral CT images can be reconstructed as virtual monoenergetic images, which are images that simulate what a CT scan image would look like if it had been obtained with monoenergetic x-rays at any given x-ray energy, such as an energy selected from 40 to 140 keV. In these virtual monoenergetic images, iodinated and barium contrast material are seen to be highly positive at low keV settings (40 to 70 keV), and gradually decrease in signal such that at high keV settings (140 keV), the signal of the iodinated and barium contrast material diminishes to that of water or soft tissue (approximately −20 to 50 HU). In other words, barium and iodine can serve as positive contrast at low keV, and neutral contrast at high keV. However, even with virtual monoenergetic images, the signal from iodinated and barium agents still cannot be differentiated from each other even with dual energy CT, which largely obviates the benefit of being able to convert the positive CT signal of contrast material to neutral CT signal. Similarly the signal of available neutral agents resemble that of water, and the signal of available negative contrast agents resemble that of fat or gas at dual energy CT, and cannot be converted meaningfully to other color signal with dual energy or spectral CT.

No commercially available enteric CT contrast material can serve simultaneously as positive, neutral, and negative contrast, even with dual energy CT.

Several clinical scenarios commonly occur in which CT diagnosis would be improved through the use of an enteric contrast medium of one type (positive, neutral, or negative) that could also be converted by image post-processing to show one or more of the other types of signal (positive, neutral or negative) at CT. For example, in suspected bowel ischemia, neutral or negative enteric contrast would be helpful to find either hyperenhancement or hypoenhancement of the bowel wall to detect inflammation or ischemia, respectively. In this same scenario positive contrast would allow identification of bowel perforation, abscesses, and fistulas. Since no commercial enteric agent can be both positive and negative, the imaging physician must choose between agents knowing that certain findings may be highlighted but other critical findings may be obscured by any available CT protocol, and hence the CT scan is suboptimal.

Development of a safe clinical enteric contrast material that can be used simultaneously with, but be differentiated from, iodinated and barium agents or other contrast agents in development such as those based on heavy metals such as tungsten, ytterbium, or tantalum would transform CT imaging for millions of patients for a wide spectrum of diseases. Multiple bodily compartments could be injected and interrogated simultaneously with a different "color" contrast agent and allow a single CT, DECT or multi-energy CT examination to provide timely high resolution perfectly co-registered anatomic images of each system for rapid and confident diagnosis. This capability will transform our ability to urgently and accurately evaluate multi-organ injury from trauma, invasive tumors, surgical complications, and inflammatory disease. Our prior patents show that low atomic number (Z<30) contrast agents or silicon-based polymer agents can provide positive CT signal that can be differentiated from iodine and barium based contrast agents at DECT.

Development of a safe clinical enteric CT contrast material that can be digitally manipulated to appear as a negative, neutral, or positive contrast material under the control of the interpreting physician would provide powerful diagnostic capability and remove guesswork and protocol errors as well as diagnostic errors. Reduced errors will result in faster diagnoses and a reduced need for additional workup. Physicians would no longer need to weigh the benefits and drawbacks of giving neutral or negative versus positive enteric contrast material for given clinical scenarios.

Non-iodinated positive contrast materials tested for use with CT imaging include a broad range of high atomic-number (Z) elements: tungsten, tantalum, ytterbium, bismuth, the lanthanides such as gadolinium, and gold, among others [Yu S, Watson A. Metal-Based X-ray Contrast Media. *Chem Rev.* 1999; 99 (9):2353-2378; and Mongan J, Rathnayake S, Fu Y, Wang R, Jones E F, Gao D W, Yeh B M. In vivo Differentiation of Complementary Contrast Media at Dual-Energy CT. *Radiology.* 2012; 265 (1): 267-272]. Silicone-based and low atomic number contrast agents have recently been invented by our group.

Dual energy CT is a relatively new technology, with practical DECT scanners only available for the past 8 years.

At clinical CT imaging, the CT number of water is defined as 0 HU while the CT number of room air/vacuum is −1000 HU, regardless of the kVp setting. The CT number of non-fat soft tissues generally ranges from 10 to 60 HU.

Examples of materials with X-ray attenuation lower than that of non-fat soft tissues include fat and oils which have CT numbers that range from −20 to −150 HU when imaged at 120 kVp. Also, the CT number of gases is generally less than −500 HU due to the very low physical density of gas.

Examples of materials with X-ray attenuation higher than that of non-fat soft tissues include solid or liquid phase materials with an effective Z greater than 8. These materials include the positive contrast materials mentioned above.

At dual energy CT, positive enteric contrast material that has a substantially different 80:140 kVp CT number ratio than iodinated or other positive intravascular contrast material can be digitally subtracted from CT images to provide images that resemble CT scans that are obtained only with intravascular contrast material. However, this signal separation can introduce some image artifacts and noise that could potentially cause diagnostic ambiguity or confusion. The highlighting of neutral or negative enteric contrast material at conventional CT is currently very difficult since the signal of such agents is not reliably differentiated from that of water, fluid, fat or gas, respectively that can occur in normal or diseased tissues.

BRIEF SUMMARY OF THE INVENTION

The present invention solves these and other problems by providing safe and effective encapsulated gas or partial vacuum particles as contrast materials suitable for human use at CT imaging, including dual energy and spectral CT. In an exemplary embodiment, the contrast material contains a particle that is an encapsulated gas or vacuum where the shell is composed primarily of silicon dioxide, silicon-containing rubber, ceramic or other inert insoluble material and the formulation is composed of encapsulated gas or vacuum particles suspended in a water or oil medium. In various embodiments, additives are added to the shell, coat the shell, contained in the lumen of the shell, or are added to the suspending medium to modulate the overall 80:140 kVp CT number ratio of the contrast material. In various embodiments, the present invention provides the benefits of negative, neutral, and positive enteric contrast at CT without the interpretation pitfalls of any of these types of enteric contrast media. In various embodiments, the present invention may appear as a negative contrast material at conventional CT, but the signal of the contrast material can be converted to even more strongly negative, neutral, or positive signal at dual energy CT or spectral CT imaging. Alternatively, in various embodiments, the present invention may appear as a positive contrast material at conventional CT, but the signal of the contrast material can be converted to negative or neutral signal at DECT or spectral CT imaging. Alternatively, in various embodiments, the present invention may appear as a neutral contrast material at conventional CT, but the signal of the contrast material can be converted to negative or positive signal at DECT or spectral CT imaging. Benefits of positive enteric contrast signal include: superior identification of enteric leaks, detection of extralumenal collections such as abscesses, detection of abdominopelvic tumors and masses, evaluation of intestinal transit time, evaluation of bowel obstruction transition point, superior evaluation for bowel wall thickening. Pitfalls of positive enteric contrast include, when concurrent intravascular contrast material is given, obscuration of critically important findings for bowel mural ischemia or bowel inflammation, obscuration of abdomenopelvic vasculature, prevention of 3D reformation for CT angiography, ambiguity as to the origin of extravasated contrast material, and obscuration of active intraluminal gastrointestinal bleeding. Benefits of negative or neutral enteric contrast include: superior evaluation of bowel mural hyper- or hypoenhancement; superior evaluation of enhancing intraluminal masses; non-interference with three dimensional reformations of CT angiograms; and lower radiation dose when CT scans are obtained with automatic exposure control owing to the lower x-ray attenuation of the negative agent on the CT scout image. Pitfalls of neutral or negative enteric contrast include reduced ability to detect bowel leakage or extralumenal fluid collections, abscesses, injury to fat, or hematomas.

At CT imaging, materials of the invention may give CT numbers that are lower or higher than the range produced by water and non-fat soft tissues (range, −20 to 60 Hounsfield Units, or HU). The combination of low and high X-ray attenuation material in substantial proportions allows for the modulation of X-ray attenuation of the new material such that 1) the new X-ray attenuation is much different than that of other bodily or medically relevant materials at CT imaging and 2) the new X-ray attenuation at different X-ray energy spectra is much different than that of other medically relevant materials at dual energy or spectral CT imaging.

For example, gas and vacuum can produce low CT signal of approximately −1000 HU, while silicon dioxide produce high CT signal of approximately 550 HU at 50% w/w suspension in water. The gas and vacuum within a silicon dioxide-encapsulated gas and vacuum particle allows the very negative CT number of the gas and vacuum to dramatically decrease the overall CT number produced by the overall particle across all CT kVp settings. This CT number reduction can be used to substantially alter the low to high kVp CT number ratio of materials to levels that are markedly different than those of iodine and barium contrast material, or of other materials that naturally occur in the human body. For example, the 80:140 kVp CT number ratio of silicon dioxide, gas, and vacuum, which are approximately 1.3, 1.0 and 1.0, respectively, can be changed to 0.3, which is substantially different than that of soft tissue (1.0) or iodine (1.7) or barium contrast material (1.7). In another example, the 80:140 kVp ratio of iodine or barium contrast material can be changed to be greater than 2.4 when encapsulated gas and vacuum particles are mixed with the iodine or barium material in a suspending medium. In another example, the 80:140 kVp number ratio of iodine or barium contrast material can be reduced to less than 0.6 when the iodine or barium is diluted and mixed with a relatively large quantity of encapsulated gas and vacuum particles.

Benefits of certain glass encapsulating shells, such as borosilicate glass, include their inertness, low solubility, stability, high strength, and very low coefficient of thermal expansion. These properties allow encapsulated gas or partial vacuum to remain stable across a broad range of physiological pH and temperature.

Enteric agents for CT are generally safer than injectable ones for several reasons: 1) Enteric agents require substantially lower doses and concentrations of material than intravascular agents. Typical intravenous iodinated agent administration requires up to 150 mL of 350 mg iodine/mL contrast (52 gram dose) for an abdominal CT scan. The typical oral dose is 800 mL of only 10 mg iodine/mL contrast (8 gram total iodine dose); 2) Very little contrast material is absorbed through the bowel wall into the vasculature; 3) Viscosity and osmolality are of minimal concern for enteric contrast materials; 4) Renal toxicity, which is seen with all intravascular agents, is unlikely with enteric agents; 5) Anaphylactoid and immune reactions are far less likely to occur with enteric than intravascular administration.

Of note, besides enteric formulation safety and CT imaging effectiveness, other aspects including physical homogeneity, storage stability, flowing ability (thus even high but acceptable viscosity), and even oral taste are among our considerations so as to optimize the final enteric contrast formulations to meet practical clinical use.

Moreover, the encapsulated gas or partial vacuum particle enteric contrast agent of the invention offers the advantage of allowing simultaneous administration of the enteric and a separate intravascular or other bodily compartment agent that can be readily differentiated by DECT or multi energy CT. Because the agents are imaged when they are simultaneously present in the body, in one embodiment, essentially perfect co-registration of images of contrast enhanced regions is provided when the signal from each agent is extracted. The well-co-registered resultant images provide superior information for diagnostic evaluation than if each contrast material were delivered and imaged separately and separate CT scans performed. Furthermore, in an exemplary embodiment, the radiation dose is half or less of what two separate scans, one with each contrast agent, would deliver. In various embodiments, the medium and formulations of the invention facilitate repeat CT scanning, reducing the ambiguity caused by previously delivered different-material based oral contrast. In various embodiments, multiple enteric agents, including the encapsulated gas or partial vacuum particle and other enteric agents, are simultaneously present at the time of CT imaging.

The formulations and method of the invention also provide the advantage of reducing radiation dose to patients due to reduced need for repeat/follow-up imaging scans.

In an exemplary embodiment, use of the invention reduces CT radiation dose compared to use of currently available positive enteric contrast material because less CT tube current is needed to generate sufficient X-ray flux to achieve diagnostic levels of image noise when the enteric contents are less radiodense (e.g. neutral or negative in CT number). For example, automated exposure control at CT may determine required X-ray tube currents based on the X-ray density of the subject in the scout view.

In an exemplary embodiment, the invention provides an agent that can be better separated at dual energy CT from both iodinated or barium contrast and from soft tissue or water than any other previously described contrast material due to the very high 80:140 kVp CT number ratio of over 2.4, or the very low 80:140 kVp CT number ratio for example less than 0.5, of various embodiments of the invention.

In an exemplary embodiment, the invention provides an encapsulated gas or partial vacuum particle in water suspension which is an enteric contrast medium formulation. An exemplary formulation comprises an enteric contrast medium comprising gas or vacuum encapsulated within a shell material to form small particles. The material is formulated in a pharmaceutically acceptable aqueous or oil-based vehicle in which the particles are suspended. In an exemplary embodiment, the shell material of the particle of the invention contains silicon and the material is a silicon-based polymer. In an exemplary embodiment, the shell material contains silicon and the material is a form of glass, such as borosilicate. In an exemplary embodiment the shell material is a polymer plastic, rubber, wax, ceramic, or resin. In an exemplary embodiment, the shell material contains or is coated with additive high atomic number material with z between 40 and 84. In an exemplary embodiment, the vehicle contains material that shows high x-ray attenuation, such as barium or iodine containing material, and thereby alters the CT number and low to high CT number ratio of the resultant contrast agent.

In an exemplary embodiment, the invention provides a contrast medium formulation that may also be delivered into the digestive system and other bodily cavities that may be natural such as the vagina or bladder, or surgically created such as neobladders, or artificial medical devices such as tubes, catheters, pouches, reservoirs, or pumps.

Additional illustrative advantages, objects and embodiments of the invention are set forth in the description that follows.

The enteric contrast agents of our invention are substantially different from microbubble contrast agents used in ultrasound imaging. Microbubbles in ultrasound are usually gas microbubbles of perfluorocarbon gas or nitrogen gas surfaced-coated by material such as albumin, carbohydrates, lipids, or biocompatible polymers that allow ultrasound to cause expansion and contraction of the bubbles to thereby amplify signal at ultrasound imaging. The mean size of ultrasound contrast microbubbles is usually in the 2-6 micron range, and the common concentration level is about 10 million microbubbles per mL. It is thus calculated that less than 1% of the volume of microbubble-type ultrasound contrast formulations is gas-filled or hollow, and such a small volume fraction of gas or void space does not produce sufficiently large signal to be useful at CT or X-ray imaging. Two recent review articles are given here:

1) Ultrasound microbubble contrast agents: Fundamentals and application to gene and drug delivery By: Ferrara, Katherine; Pollard, Rachel; Borden, Mark. Book Series: ANNUAL REVIEW OF BIOMEDICAL ENGINEERING Volume: 9 Pages: 415-447 Published: 2007; 2) Microbubbles in medical imaging: current applications and future directions. By: Lindner, J R. NATURE REVIEWS DRUG DISCOVERY, Volume: 3 Issue: 6 Pages: 527-532 Published: June 2004

The enteric CT contrast materials of the present invention are substantially different than previous perfluorocarbon oral contrast materials proposed for CT and MR and X-ray imaging. These previous agents include liquid perfluorocarbon, which may or may not be emulsified; the perfluorocarbon may or may not be brominated. In these previous agents, the perfluorocarbon may expand into a gas at body temperature and create negative contrast signal and further bowel distension. Drawbacks of perfluorocarbon agents are that they may be difficult to administer, and their expansile characteristic carries safety concerns when administered into diseased bowel segments (U.S. Pat. Nos. 5,205,290; 4,951,673; Spilde et al., "Evaluation of an Experimental Low-Attenuation Gastrointestinal Contrast Agent for CT Imaging of Intestinal Ischemia in an Animal Model". *Acad. Radiol.* 1999; 6:94-101.) Brominated perfluorocarbons have been described as CT contrast agents and may produce positive CT number signal.

Other embodiments, objects and advantages of the invention will be apparent from the detailed description that follows.

BRIEF DESCRIPTION OF THE DRAWINGS

FIG. 7. CT number values correspond to images of contrast materials of FIG. 6.

FIG. 10. Examples of previously patented or disclosed agents with high 80:140 kVp CT number ratios created by combining hydrocarbons with high x-ray attenuating materials such as iodinated or silicon-containing compounds. While high 80:140 kVp CT number ratios could be achieved by the prior methods, the encapsulated gas materials of our invention provide a wider range of possible 80:140 kVp CT number ratios, including ratios lower than 0.9 (see FIG. 11). Note: by definition water has a CT number of approximately 0 HU at all kVp settings.

FIG. 11. Examples of mixing high x-ray attenuating materials with gas or partial vacuum to generate materials with 80:140 kVp CT number ratios far beyond the range of 1.0 to 1.8. The CT numbers and the 80:140 kVp CT number ratios of materials can be substantially changed when substantial amounts of gas are combined with high x-ray attenuating materials.

FIG. 12. Table of CT numbers at virtual monoenergetic dual energy or spectral CT image reformations for example low x-ray attenuating material (gas/vacuum), high x-ray attenuating materials, and encapsulated gas or partial vacuum particles with high x-ray attenuating material shells. By definition, the CT number of pure water is set as 0 HU at all virtual monoenergetic image reformations.

FIG. 13. Table of CT numbers at different kVp tube potential settings, and at dual energy CT virtual monoenergetic CT settings, of example high x-ray attenuating materials, encapsulated gas or partial vacuum particle formulations, and further additions of other high x-ray attenuation materials to the formulations. Note: the CT number of gas/vacuum in these cases is approximately −1000 HU.

FIG. 14. Table of potential benefits of encapsulated gas or partial vacuum particle contrast material compared to commercial and previously described enteric CT contrast agents.

FIG. 15. Hollow microsphere-based contrast materials show similar CT number and 80:140 kVp CT number ratios when scanned on General Electric (GE) and Siemens CT scanners. CT numbers were measured at CT tube potentials of 80, 100, 120, and 140 kVp on commercial clinical dual energy CT scanners. For General Electric, the scanner was a 750 HD. For Siemens, the scanner was a Somatom Definition. The Readi-cat® contrast material contains 2.1% w/v barium sulfate in aqueous suspension. The borosilicate hollow microspheres are 3M products (iM30K). The favorable, high or low 80/140 kVp CT number ratios of these exemplary contrast material formulations of our invention were similar when imaged on the two commercial dual energy CT scanners from different CT scanner manufacturers.

FIG. 17. Examples of encapsulated gas or partial vacuum particles in 30% w/w suspension in water, with corresponding CT numbers at 80 and 140 kVp. A remarkably wide range of CT numbers and wide range of 80:140 kVp CT number ratios are achieved, depending on the shell composition and thickness.

DETAILED DESCRIPTION OF THE INVENTION

I. Introduction

Figure 1:
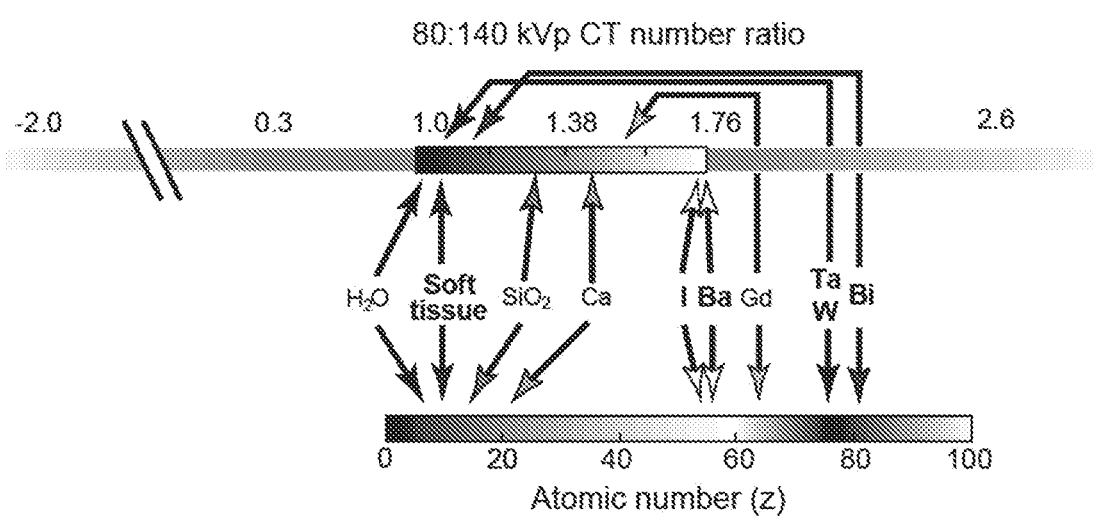
FIG. 1 is a computer simulation of 80:140 kVp CT number ratios (Gray scale from black to white, top side, within black outlined box) for individual atoms with range of atomic number (Z, bottom side) from 1 to 100. This simulation was based on the expected CT x-ray tube output spectrum of a typical clinical CT scanner and the National Institute of Standards and Technology x-ray attenuation coefficients of the individual elements. This simulation correctly predicts that conventional iodine- and barium-based CT contrast agents (I and Ba, respectively) have high 80:140 kVp CT number ratios of approximately 1.7, that calcium based materials such as bone have intermediate 80:140 kVp CT number ratios of slightly over 1.4, and that silica (Sift) has an intermediate 80:140 kVp CT number ratio of about 1.27. However, this atom-based model did not apparently predict that materials would have a very high 80:140 kVp CT number ratio over 1.8 or less than 0.9 or negative number (top side, gray scale gradient outside of black outlined box). Our prior finding (WO2015/024025A1) that silicon-based polymer, exemplarily polydimethylsiloxane (PDMS), has such a high 80:140 kVp CT number ratio (2.6-2.8) was not anticipated initially by ourselves. Similarly, our finding that encapsulated gas or partial vacuum particles could provide a wide range of 80:140 kVp CT number ratios from less than 0.8, including ratios that are negative or well over 2.0, which are far beyond the range predicted by the initial computer simulation, was not anticipated either.
Figure 2:
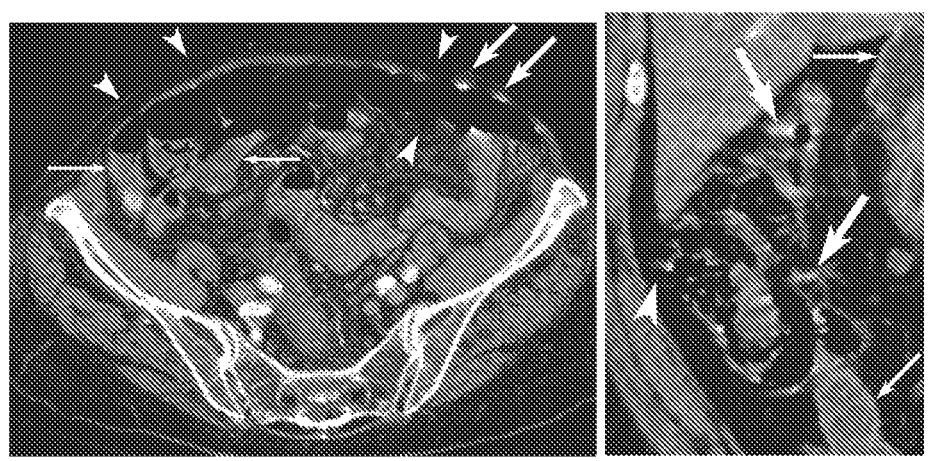
FIG. 2. Transverse (left image) and coronal (right image) CT images show motion artifact around gas-filled bowel (black intraabdominal structures) but not around fluid filled bowel (small arrows). The intralumenal bowel gas is highly negative in CT number (−950 to −1005 HU) and may cause artifact that can be bright (large arrows) and dark signal (arrowheads) around the bowel.
Figure 3A:
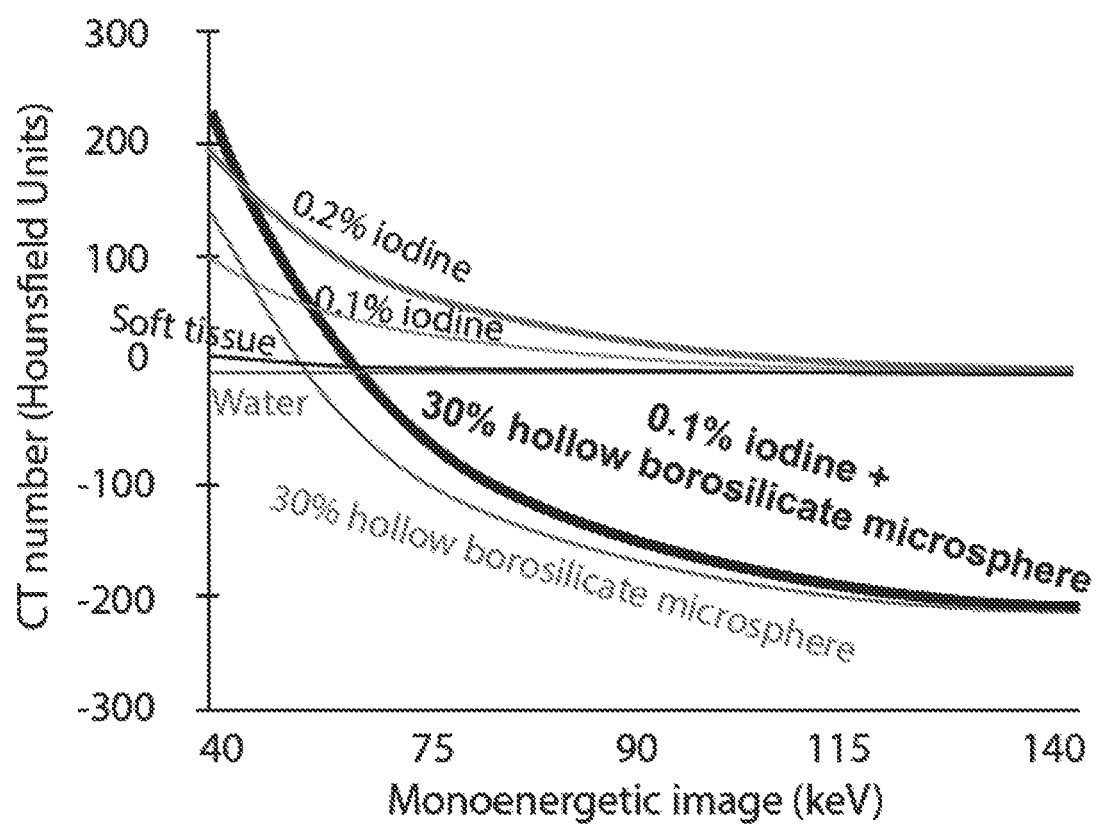
FIG. 3A-FIG. 3B. Adjustment of CT numbers of borosilicate encapulated gas and partial vacuum microsphere suspensions by addition of heavy metal. A) Heavy metal addition to the aqueous suspension: The CT numbers of aqueous suspensions of borosilicate encapsulated gas and partial vacuum microsphere particles (specific gravity 0.6 g/mL) with or without added high x-ray attenuation material (0.1% iodine in the aqueous medium) are shown. The combination of the two materials yields a new contrast agent with much higher CT number at low virtual monoenergetic keV and a steeper slope of signal loss at low to high keV. This new contrast material provides strongly negative CT signal when the virtual monoenergetic keV is greater than 75, and strongly positive CT signal when the virtual monoenergetic keV is less than 55. The borosilicate microsphere suspension alone does not provide as high a signal as the iodine and borosilicate microsphere combination formulation. Addition of more iodine or barium to the formulation allows for upward adjustment of the CT number signal at the lower monoenergetic keV levels (not shown). B) Heavy metal addition into the particle. The CT numbers of two 20% wt/wt aqueous suspensions of different borosilicate encapsulated gas and partial vacuum microsphere particles (specific gravity 0.50 g/mL), one with and the other without 0.5% barium incorporated into the shell material, are shown. Again the addition of barium causes an increase in CT number measurements predominantly at the lower virtual monoenergetic keV CT image range. In this example, the CT number for the barium-doped microsphere suspension becomes positive at 40 keV, while it remains strongly negative at keV's higher than 60 keV. Different results can be obtained with different types and quantities of heavy metals (not shown).
Figure 3B:
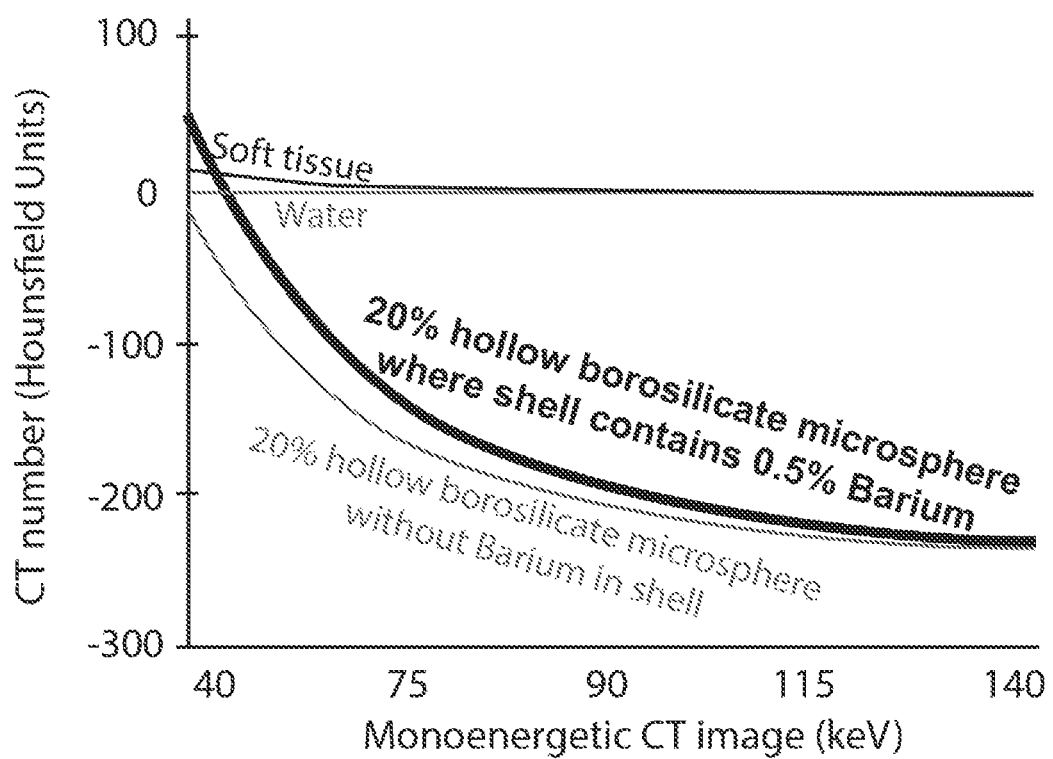
Figure 4:
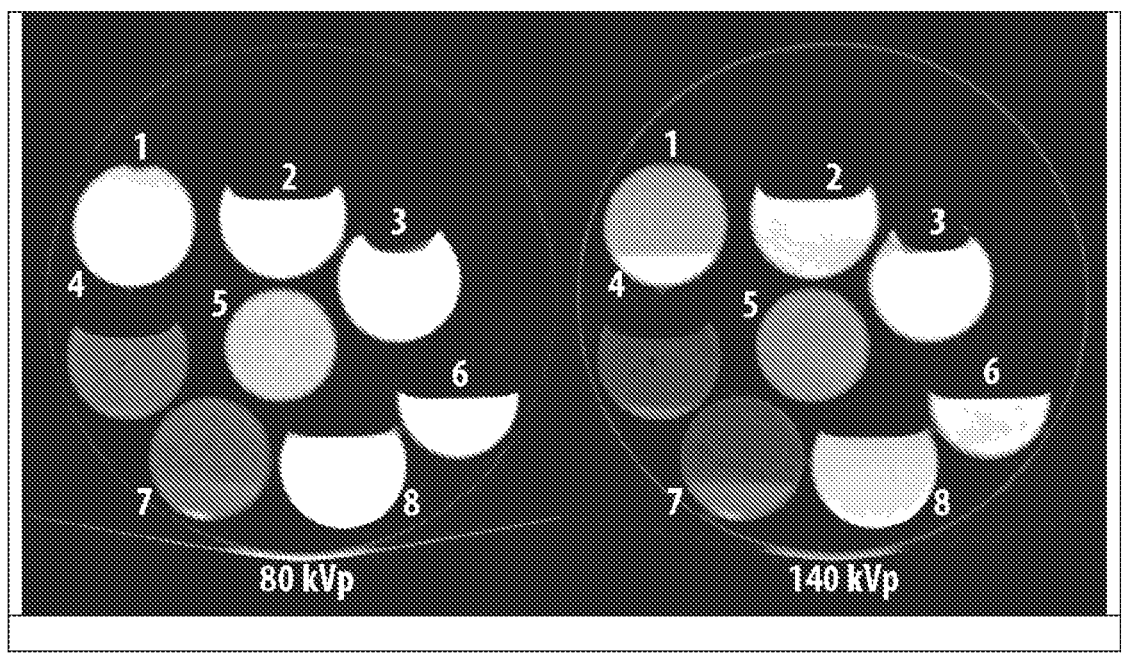
FIG. 4. Conventional CT scans of different vials of materials, imaged at 80 (left) and 140 kVp (right image). 1=iM30K 18 micron hollow silica microspheres a 30% w/w with 15 mg I/mL iohexol in water; 2=Pepto-bismol® bismuth salicylate; 3=iodine (15 mg I/mL iohexol) in water; 4=iM30K 18 micron hollow silica microspheres at 40% w/w in water; 5=1% barium w/w and 30% iM30K w/w with sorbitol and water; 6=2% BaSO4 (Readi-Cat2®) (contains sorbitol in water); 7=S60HD 30 micron silica microspheres at 40% w/w in water; 8=2% Barium Sulfate in water. The partially suspended hollow silica microspheres (#4 and 7) are less radiodense than water at 80 and 140 kVp, with even lower signal at 140 than at 80 kVp. Layering of water, which is physically higher specific gravity than the hollow silica micropsheres, is seen at the bottom of both of these vials. A small amount of high x-ray attenuating material, representing non-hollow borosilica, is in the bottom of the S60HD vial. In vial #1, the iohexol is uniformly dissolved in the water, which layers at the bottom of the vial. The iodine and barium contrast materials (#3, 6, and 8) each show decreased signal from 80 to 140 kVp. The tubes with hollow silica microspheres mixed with iodine (1) and barium (5) show very substantial relative drop in CT signal from 80 to 140 kVp. The 80:140 kVp CT number ratio for the iodine silica microsphere mixture was 2.8, and for the barium silica microsphere was 4.1. Bismuth material (Pepto-bismol®) shows relatively little change in CT number between 80 and 140 kVp.
Figure 5:
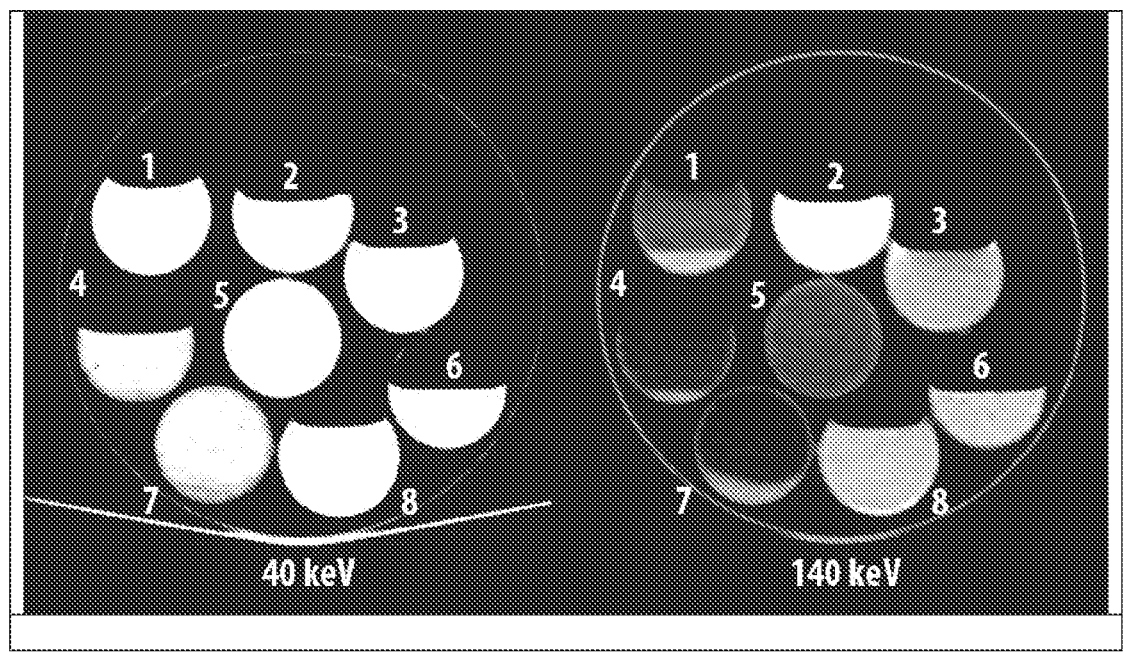
FIG. 5. Dual energy CT scans of different materials, reconstructed at virtual monoenergetic 40 keV (left) and 140 keV (right image). 1=iM30K 18 micron hollow silica microspheres a 30% w/w with 15 mg I/mL iohexol in water; 2=Pepto-bismol® bismuth salicylate; 3=iodine (15 mg I/mL iohexol) in water; 4=iM30K 18 micron hollow silica microspheres at 40% w/w in water; 5=1% barium w/w and 30% iM30K w/w with sorbitol and water; 6=2% BaSO4 (Readi-Cat2®) (contains sorbitol in water); 7=S60HD 30 micron silica microspheres at 40% w/w in water; 8=2% Barium Sulfate in water. The partially suspended hollow silica microspheres (#4 and 7) show loss of signal from 40 keV to become very low signal at 140 keV. Layering of water, which is heavier than the silica micropsheres, is seen at the bottom of these tubes. In vial #1, the iohexol is uniformly dissolved in the water, which layers at the bottom of the vial. The iodine and barium contrast materials (#3, 6, and 8) each show decreased signal from 40 keV to 140 keV such that the signal resembles that of water at 140 keV. The tubes with silica microspheres mixed with iodine (1) and barium (5) show substantial drop in CT signal on the 140 keV images such that the CT numbers are less than −100 HU on 140 keV image reconstructions. Bismuth material (Pepto-bismol®) shows relatively little change in CT number between 40 and 140 keV.
Figure 6:
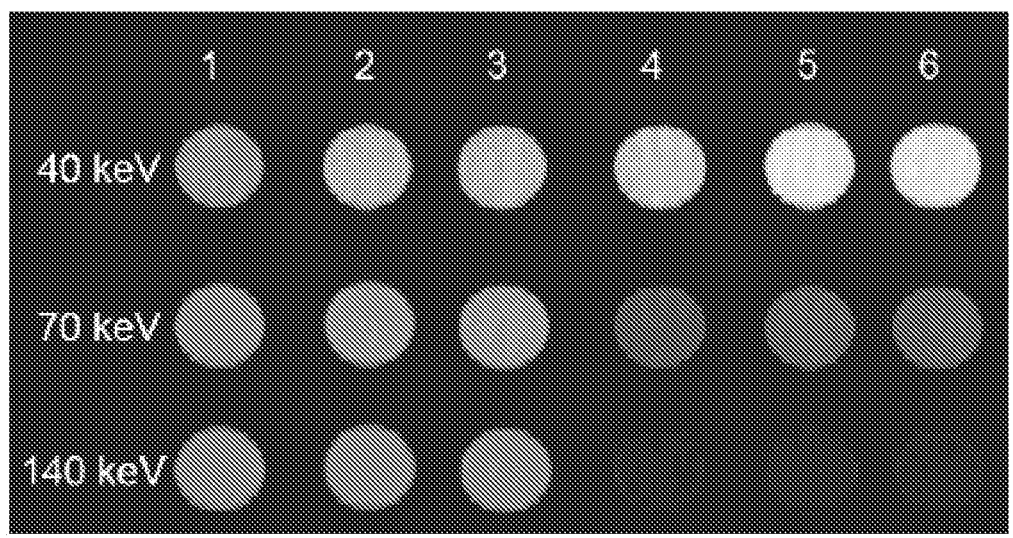
FIG. 6. Contrast materials imaged at dual energy CT with virtual monoenergetic image reformations at 40, 70 and 140 keV. 1=water; 2=0.1% iodine solution; 3=0.1% barium suspension; 4=borosilicate hollow microsphere 30% w/w in water; 5=0.1% iodine solution with 30% w/w borosilicate hollow microspheres in water; 6=0.1% iodine solution with 30% w/w borosilicate hollow microspheres in water. The water does not change appreciably in CT number across the monoenergetic reformations. The iodine and barium in water show slightly higher CT numbers at low than at high keV. The borosilicate hollow microspheres in water show positive signal at the low keV and negative signal at the high keV reformations. When 1% iodine or 1% barium are added to the mixture of borosilicate hollow microspheres, the CT numbers are substantially increased at low keV.
Figure 8:
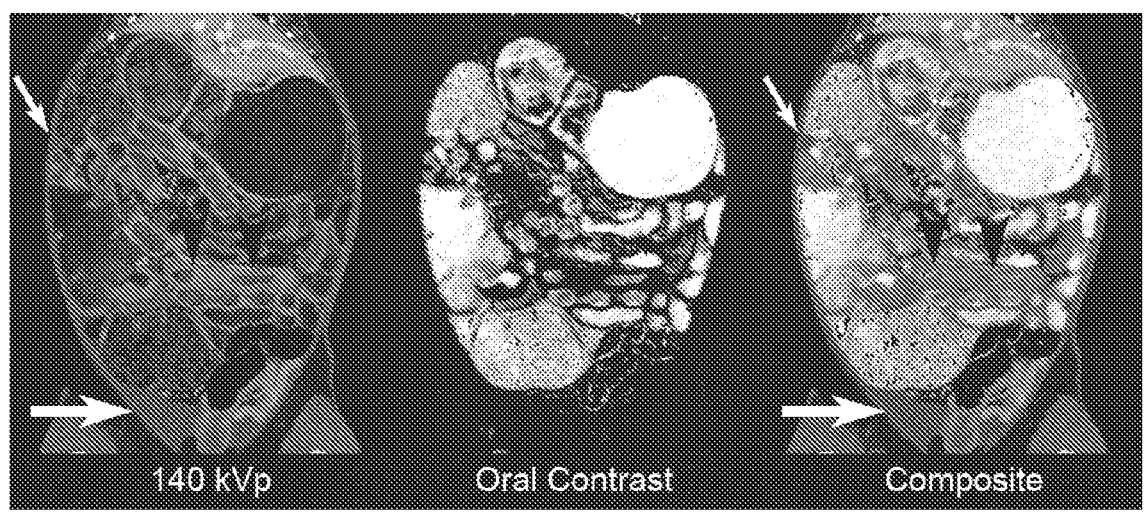
FIG. 8. 3.8 kg rabbit imaged at dual energy CT with 300 mL enteric 30% wt/wt borosilicate hollow microspheres and intravenous iodinated contrast agent. The bowel wall enhancement, for example of the rabbit cecum (arrowheads), is seen well at 140 kVp (left image) to show the intravenous iodinated contrast, but the small hematoma (thin arrow) and free fluid (large arrow) are not seen well. Two material decomposition with threshold of −50 HUs was performed to extract the signal from the enteric contrast agent, then the signal was inverted and doubled to produce the positive signal seen in the Oral Contrast image (middle image. Note that this image does not show signal from soft tissues, fat, nor iodinated contrast. The Oral Contrast signal was then added back to the 140 kVp image to generate a Composite image. Now the hematoma (thin arrow, right image) and free fluid (large arrow) are more vividly displayed. As with any image with positive enteric contrast, the enhancement of the bowel wall by intravenous contrast material is obscured in segments of bowel containing positive contrast material signal. The separation of signal from the enteric and intravenous contrast agents in this example cannot be obtained if only conventional iodinated and barium agents were utilized.
Figure 9:
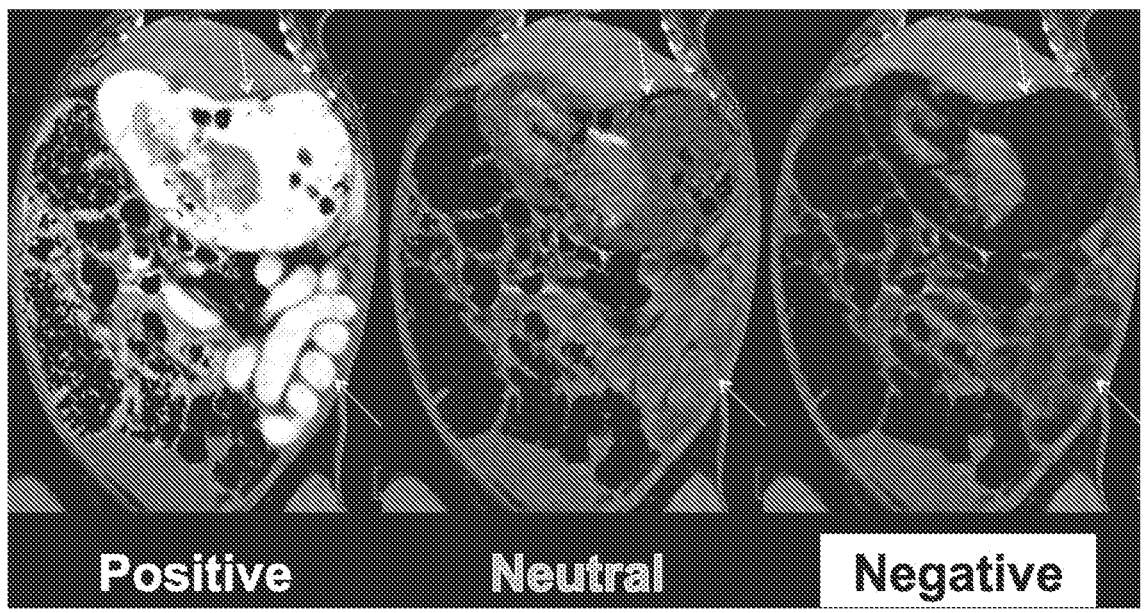
FIG. 9. 3.9 kg rabbit imaged at dual energy CT with 300 mL enteric 30% wt/wt borosilicate hollow microspheres doped with a small amount of barium sulfate and with intravenous iodinated contrast agent. The bowel lumen signal can be made to be intensely positive (left image) by use of low virtual monochromatic images (40 keV), or neutral (middle image) by use of intermediate virtual monochromatic images (65 keV), or negative (right image) by viewing with high virtual monochromatic images (100 keV). Note that the fluid in the bladder (bottom of image) and soft tissue such as the liver (top of image) do not change signal substantially across the different virtual monoenergetic keVs.
Figure 16:
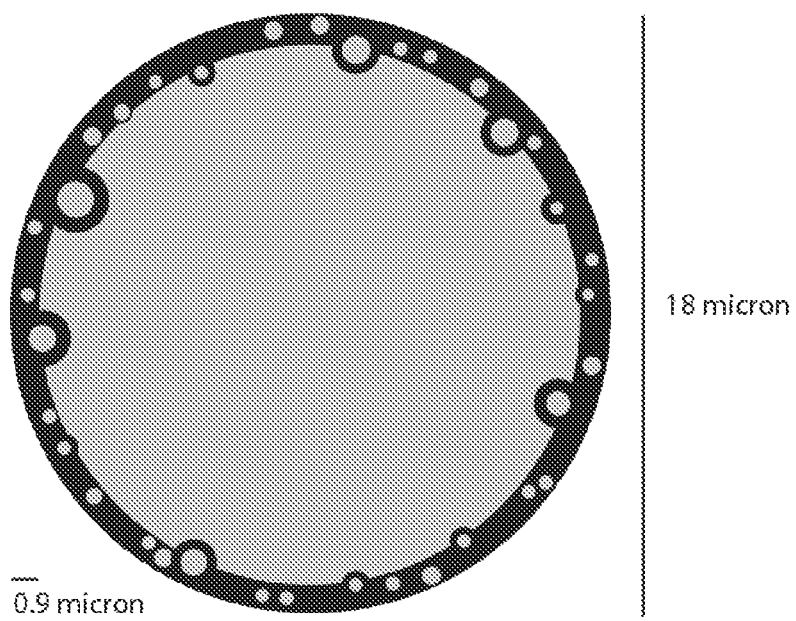
FIG. 16. An exemplary hollow borosilicate glass microsphere (e.g, iM30K from 3M Inc) is shown in this schematic. The density of this exemplary microsphere is 0.60 g/cm$^3$ and average diameter is 18 microns. By comparison, the density of bulk borosilicate glass is 2.4 g/cm$^3$. Roughly 75% of the volume of the borosilicate glass microsphere is hollow (gas-filled or partial vacuum, shown in gray). The shell material (black color) has an average thickness of about 10% of the radius of microsphere, and is approximately 0.9 microns thick. Small imperfections of trapped gas and partial vacuum may exist in the shell material. In an exemplary embodiment of the invention, suspending agents are used to maintain the hollow microspheres in an aqueous formulation, in the presence or absence of additional high-Z contrast (iodine or barium material), to produce useful enteric contrast materials with favorable CT number for use with single energy spectrum CT and with favorable 80/140 kVp CT number ratio for use with dual energy or spectral CT. The shell may or may not have small imperfections within it. The overall particle may have a dominant hollow space, or may be subdivided by septations of shell material.
Figure 18:
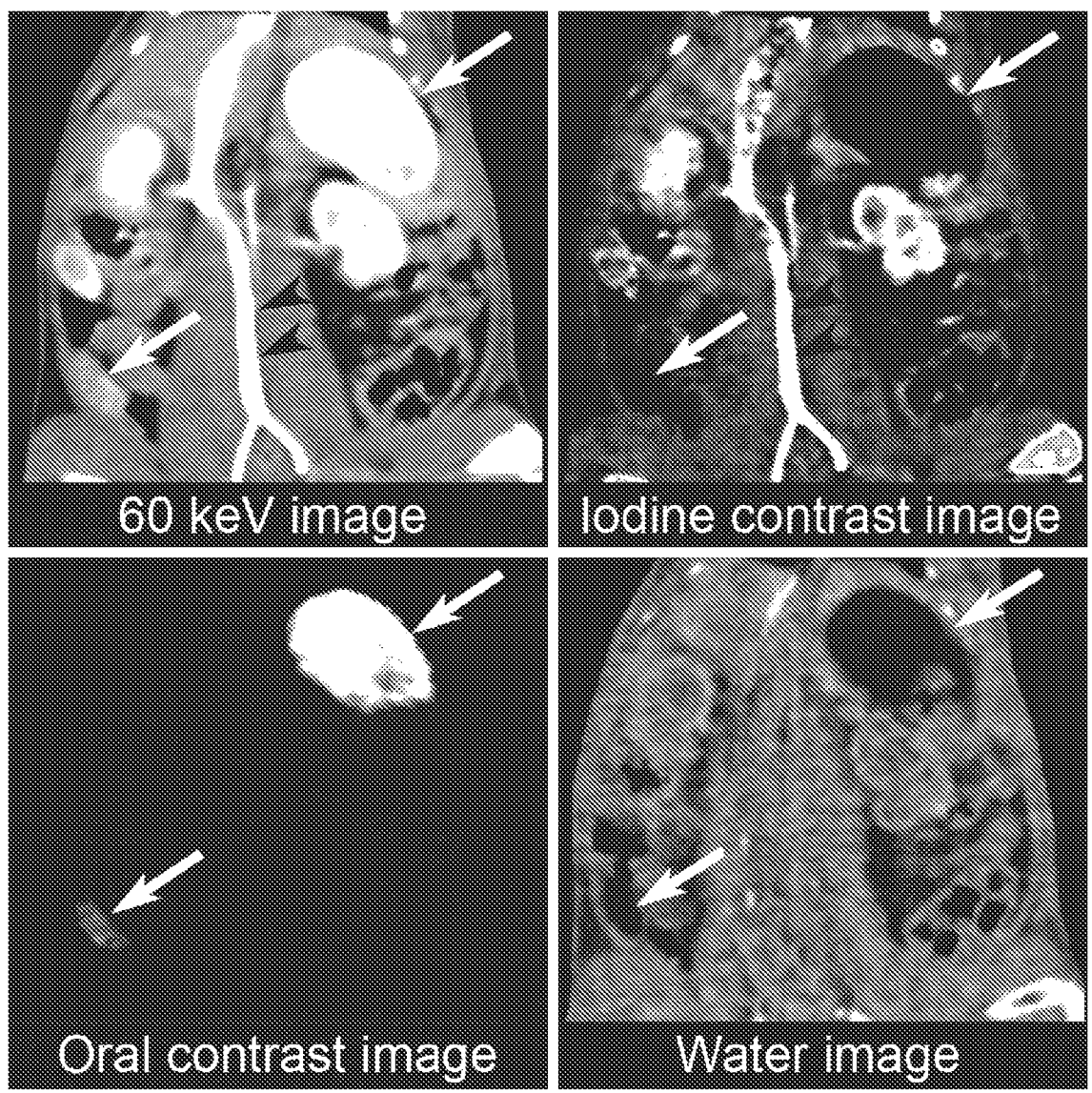
FIG. 18. Coronal dual energy CT images of rat with intravenous iodinated contrast material (black arrowheads) and exemplary enteric formulation of the invention (white arrows). The enteric formulation is 30% w/w encapsulated gas and partial vacuum borosilicate microspheres (iM30K, 3M) with 2.5% w/w iodine (iohexol, General Electric Healthcare) suspended using sorbitol and methylcellulose. The 60 keV image is the virtual monochromatic image obtained from the CT scanner. Three material decomposition was performed using the 40 and 140 keV virtual monochromatic images as source data to produce the iodine contrast image, oral contrast image, and water image. The iodine image shows the positive signal from the iodine contrast without the signal of the enteric agent. The oral contrast image shows the positive signal of the enteric agent without that of the intravenous agent. The water image simulates an unenhanced CT scan without either agent.
Figure 19:
FIG. 19. Transverse dual energy CT images of bowel necrosis in a rabbit abdomen imaged with intravenous iodinated contrast material and exemplary enteric formulation of the invention. The anterior bowel was rendered necrotic by percutaneous microwave ablation (12 minute ablation at 65 watts using 17 g P15 antenna, Certus 140 generator, NeuWave, Madison, WI). The enteric contrast formulation is 30% w/w encapsulated gas and partial vacuum borosilicate microspheres (iM30K, 3M) suspended using 0.3% xanthan gum in water. The 140 kVp image (left image) shows normal bowel wall enhancement by intravenous contrast for the bowel in the left and right abdomen. The bowel lumen (asterisk) is filled with negative contrast material that measures −60 HU, which is similar in signal to that of retroperitoneal fat which measures −80 HU in this example. In the central anterior abdomen, decreased bowel wall enhancement is seen (arrows), suggesting necrosis. The 40 keV virtual monoenergetic image (right image) more vividly shows that the central anterior bowel walls do not enhance with intravenous contrast. The absence of bowel wall enhancement confirms bowel wall necrosis of these bowel segments. By contrast, the bowel in the left and right abdomen show normal bright intravenous contrast enhancement at 40 keV. The signal of the bowel lumen contrast material is 45 HU at 40 keV. By contrast, the retroperitoneal fat is approximately is −150 HU on this 40 keV image. In other words, even though the enteric contrast material and retroperitoneal fat have similar HU values at 140 kVp, the two materials are shown to be different at the dual energy CT 40 keV image. Of note, even though the enteric contrast material is negative signal, no substantial artifact is seen around the bowel filled with this negative contrast material. However, bright artifact is seen adjacent to a gas-filled segment of bowel (thin arrow). Relative absence of bowel gas image artifact is a benefit of the negative enteric contrast of our invention over that of unencapsulated gas negative enteric contrast (see FIG. 2).
Figure 20:
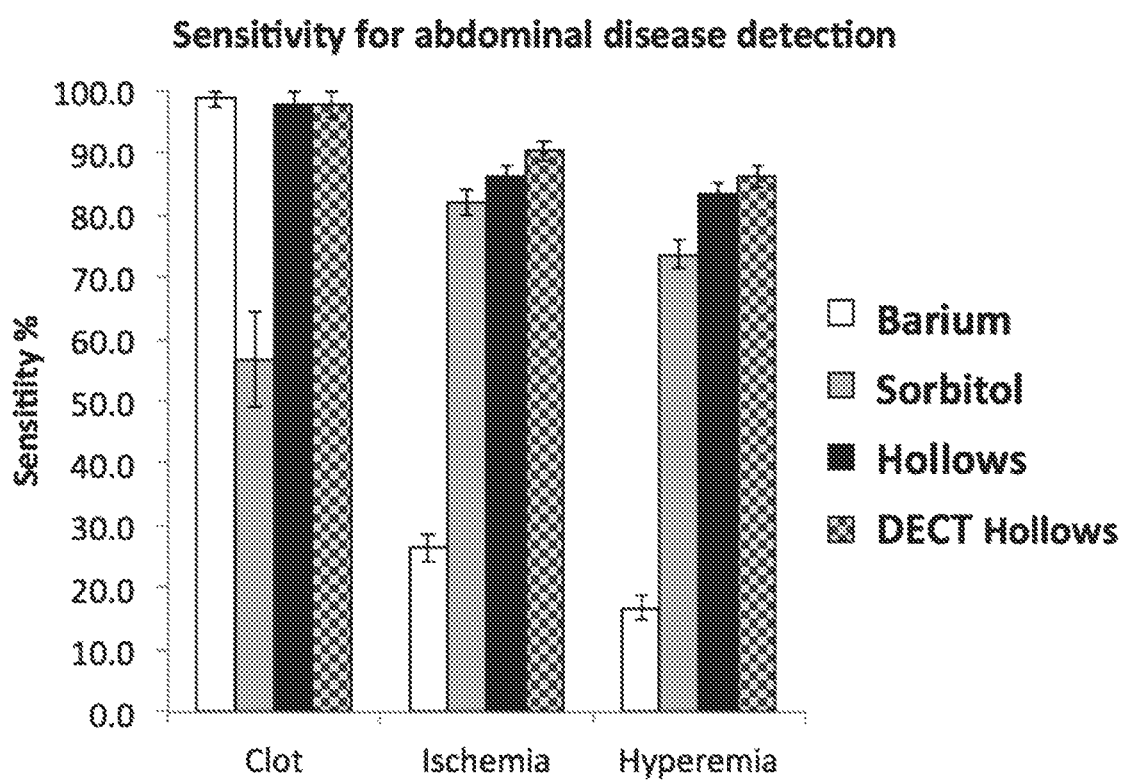
FIG. 20. Improved sensitivity for abdominal disease at CT and Dual Energy CT with encapsulated gas and partial vacuum borosilicate microsphere enteric contrast material compared with commercially available enteric contrast agents. Three enteric contrast agents were compared in rabbit models of abdominal disease imaged at intravenous iodine contrast-enhanced CT: positive contrast barium sulfate 2% w/w (ReadiCat2, Bracco); neutral contrast sorbitol solution (VoLumen, Bracco); and negative contrast hollow encapsulated gas and partial vacuum borosilicate microsphere ("Hollow", iM30K, 3M). The negative contrast encapsulated gas and partial vacuum agent was also post-processed with dual energy CT ("Hollow DECT") to produce additional images with positive and neutral appearances of the enteric contrast signal. Rabbit abdomens were implanted with ~2 cm hematomas, or underwent focal microwave ablations to create areas of bowel ischemia or bowel hyperemia. Lesions were confirmed at gross and microscopic pathology. Six radiologists reviewed each set of images on a DICOM viewer to detect the abdominal lesions. The sensitivity for hematomas was nearly perfect when positive barium or negative hollow enteric contrast was used (with or without DECT post-processing), but was only 57% with the neutral agent. Conversely, reader sensitivity for bowel ischemia or hyperemia was only 26 and 17%, respectively, for positive barium contrast, but was 82 and 73%, respectively for neutral sorbitol contrast, and was even higher for the negative hollow enteric contrast. Addition of DECT post-processing improved the sensitivity still further for the detection of bowel ischemia and hyperemia. The specificities of the different enteric contrast agents for each type of abdominal lesion were all over 94%.

A critical problem for current enteric contrast for CT is that each type (positive, negative, and neutral) only reliably differentiates a subset of the critical anatomy needed for various CT diagnoses. The positive enteric contrast material can mark the bowel lumen with bright signal which allows differentiation of bowel from fluid collections and diseased non-bowel tissue, but the positive signal cannot be differentiated from the positive signal from intravenous contrast materials. The neutral enteric contrast materials allow visualization of bowel wall enhancement by positive intravenous contrast agents, but resemble soft tissue and fluid at CT. The negative enteric contrast agents so far described are not FDA approved. These negative enteric contrast agents show all of the above anatomy and positive intravenous contrast agent signal well, but may cause unwanted side effects, may be inconvenient to administer, and can cause artifact at CT.

At any type of clinical CT, some degree of separation of contrast materials from other contrast materials and soft tissues can be obtained by use of a CT number threshold. For example, CT numbers >80 HU are unlikely to be produced by normal soft tissues, and CT numbers <−20 HU are unlikely to be produced by normal soft tissues, except for fat. Positive contrast materials that give CT numbers greater than 80 HU are readily identified as non-soft tissue material. Similarly, negative contrast materials that are less than −20 HU can be identified reliably as non-soft tissue material, with the exception that fat can give similar CT numbers. Notably, fat is rarely a concerning pathologic process in the bowel lumen.

Alternatively, at dual energy or spectral CT, materials can be differentiated based on their relative attenuation of low versus high energy X-rays. Dual energy and spectral CT are an increasingly common capability of modern scanners. Current dual energy technology allows simultaneous imaging of patients with X-rays of two or more different energy spectra, such as provided by two or more different tube potentials (such as 80 and 140 kVp, or alternatively 100 and 140 kVp). Dual energy and spectral CT imaging can also be acquired using other methods, including sandwich detectors, split beam x-rays filtered by different materials, or photon counting which quantify or classify the energy of x-rays that are seen by the detector. Materials in the body are differentiated based on their high to low tube potential CT number ratios (e.g. 80:140 kVp CT number ratios), which are related to the atomic numbers of the atoms in the material and their physical density. A simulation of CT number ratios for a clinical CT scanner shows that iodine and barium exhibit high 80:140 kVp CT number ratios of approximately 1.7, which is near the maximum value predicted for any given element on the periodic table for current clinical scanners, with CT numbers measured by the Hounsfield Unit (HU). Materials with more widely different ratios are more clearly differentiated by DECT, hence iodine and barium can be differentiated quite well from water or most soft tissues, which have 80:140 kVp CT number ratios of about 1.0. The signal from materials with intermediate 80:140 kVp CT number ratios (1.25 to 1.45) can be somewhat differentiated from that of both water or most soft tissues as well as iodinated or barium contrast material by the use of two-, three-, or multi-material decomposition algorithms. The signal from materials with very high or very low 80:140 kVp CT number ratios (>2.1 or <0.6, respectively) are better separated from the signals of soft tissue and iodinated contrast material. The enteric contrast agents of our invention can be adjusted to have these very high or very low or even negative 80:140 kVp CT number ratios.

At single energy spectrum CT, the signal from certain of the positive enteric contrast materials of our invention may be difficult to distinguish from that of positive intravenous iodinated or other heavy atom contrast agents. However, at dual energy or spectral CT, the signal from the positive enteric contrast materials of our invention are easily distinguished from iodinated intravenous contrast material because the 80:140 kVp CT number ratio of the positive enteric contrast of our invention can be chosen to be substantially different (e.g. >2.1 or below 0.9) than that of iodinated contrast (1.7 to 1.8) or other heavy atom contrast agents (0.9 to 1.3).

At single energy spectrum CT, the signal from certain of the neutral enteric contrast materials of our invention is easily differentiated from intravenous positive contrast material, but may be difficult to distinguish from water, biological fluids, or soft tissue, much like the currently available neutral enteric agents. However, at dual energy or spectral CT, the signal from the neutral enteric contrast materials of our invention can be easily distinguished from water, biological fluids, or soft tissue because the 80:140 kVp CT number ratios can be chosen to be less than 1.0 or greater than 1.8 such that they are substantially different than that of water, soft tissue or iodine contrast material (~1.0, ~1.0, and ~1.7 to 1.8, respectively).

At single energy spectrum CT, the signal from the negative enteric contrast materials of our invention may be difficult to distinguish from fat but is distinguishable from all other tissues and intravenous contrast agents. However, at dual energy or spectral CT, the signal from the negative enteric contrast materials of our invention can be easily distinguished from fat because the 80:140 kVp CT number ratios can be chosen to be less than 1.0 or greater than 1.5 such that it is substantially different than that of fat (~1.2).

Encapsulated gas or partial vacuum organic polymer particles have been previously described as a contrast material for CT (for example, encapsulated fluorocarbons, which may produce positive or negative signal at CT, and negative signal at MR imaging) (U.S. Pat. No. 5,205,290). There is, however, no prior description of encapsulated gas or partial vacuum microparticles chosen such that the shell material contributes substantially (e.g., at least about 30 HU) to the CT number (Hounsfield Unit) itself. Similarly, there is no prior description of encapsualted gas or partial vacuum microparticles chosen in which the shell material provides a subsantial CT number difference when the microparticle formulation is imaged at low versus high X-ray tube potential (e.g., 80 versus 140 kVp). Encapsulated gas particles have been described as contrast agents for ultrasound, but these agents resemble water signal at CT and do not exhibit 80:140 kVp CT number ratios substantially different than those of water and soft tissue.

Historically, positive contrast agents for CT have predominantly used a single high x-ray attenuating element, such as iodine in iodinated contrast agents or barium in barium sulfate agents, as the reporter atom to generate contrast signal. Addition of gas or partial vacuum to high x-ray attenuating materials to modulate the signal of the resultant material for use with CT, including dual energy or spectral CT, has not been previously described. In various embodiments, our invention utilizes gas or partial vacuum to modulate the signal of our overall contrast agent formulation to improve its value for CT and for dual energy or spectral CT as a contrast agent.

Historically, CT contrast agents that used gases did not utilize other elements to modulate the gas signal at CT. Gas-filled microsphere contrast agents, including fluorocarbon contrast agents, did not utilize shell material to substantially change the CT number of the encapsulated gas, and did not utilize shell material that substantially changed the 80:140 kVp CT number ratio of the encapsulated gas. In various embodiments, our invention utilizes other non-gas atoms and molecules to modulate the signal produced by gases and vacuum at CT to improve their value for CT and for dual energy or spectral CT as a contrast agent.

Our invention, in various embodiments, provides for CT contrast agents with one or both of the following properties: 1) substantially different CT signal (CT number) than important soft tissues or intravenous contrast agents; and 2) substantially different low to high kVp CT number ratio than important soft tissues, fat, or intravenous contrast agents.

II. Definitions

Unless defined otherwise, all technical and scientific terms used herein generally have the same meaning as commonly understood by one of ordinary skill in the art to which this invention belongs. Generally, the nomenclature used herein and the laboratory procedures in organic chemistry, pharmaceutical formulation, and medical imaging are those well known and commonly employed in the art.

The articles "a" and "an" are used herein to refer to one or to more than one (i.e. to at least one) of the grammatical object of the article. By way of example, "an element" means one element or more than one element. Contrast agents with iodine, barium or other atoms with Z greater than 40 are exemplary "high Z" materials.

A "disease" is a state of health of an animal wherein the animal cannot maintain homeostasis, and wherein if the disease is not ameliorated then the animal's health continues to deteriorate.

"Contemporaneous" administration refers to use of a contrast agent in conjunction with a medical imaging procedure performed on a subject. As understood by one of skill in the art, contemporaneous administration of the contrast agent to the subject includes administration during or prior to the performance of the medical imaging procedure such that the contrast agent is visible in the medical image of the subject.

The term "half-life" or "t ½", as used herein in the context of administering an enteric contrast medium of the invention to a patient, is defined as the time required for enteric concentration of a drug in a patient to be reduced by one half. There may be more than one half-life associated with the contrast medium depending on multiple clearance mechanisms, redistribution, and other mechanisms well known in the art. Further explanation of "half-life" is found in Pharmaceutical Biotechnology (1997, D F A Crommelin and R D Sindelar, eds., Harwood Publishers, Amsterdam, pp 101-120).

"Enteric contrast medium formulation" as herein used means, unless otherwise stated, a pharmaceutically acceptable liquid or paste formulation for administration to a subject, which comprises at least one enteric contrast medium, and with or without at least one pharmaceutically acceptable excipient suspending the medium, and which is prepared by dissolving, emulsifying, or suspending an enteric contrast medium as herein described, e.g. in the form of a powder, emulsion or mash, in a pharmaceutically acceptable vehicle, before use for administration to the subject. Preferably the suspending medium is water.

The term "residence time", as used herein in the context of administering an enteric contrast medium to a patient, is defined as the average time that the enteric contrast medium stays in the body of the patient after dosing.

The term "dual energy or spectral CT" refers to CT imaging where the detectors record X-ray flux that are of at least two different X-ray spectra. The X-ray spectra may be generated prior to the X-rays penetrating the imaged object, such as may occur with different X-ray sources set at different tube potentials, filtered with different materials, or a given X-ray source that switches between different tube potentials. Alternatively, the X-ray spectra may be separated after penetrating the imaged object objects, such as may be obtained by the use of layered detector arrays or by photon counting detectors.

As used herein, "pharmaceutically acceptable carrier" includes any material, which when combined with the conjugate retains the activity of the conjugate activity and is non-reactive with the subject's immune system. Examples include, but are not limited to, any of the standard pharmaceutical carriers such as a phosphate buffered saline solution, water, emulsions such as oil/water emulsion, and various types of wetting agents. Other carriers may also include sterile solutions. Typically such carriers contain excipients such as starch, milk, sugar, sorbitol, methylcellulose, certain types of clay, gelatin, stearic acid or salts thereof, magnesium or calcium stearate, talc, vegetable fats or oils, gums, glycols, or other known excipients. Such carriers may also include flavor, texture, and color additives or other ingredients. Compositions comprising such carriers are formulated by well known conventional methods.

As used herein, "administering" means oral administration, administration as a suppository, topical contact, intrarectal, intravenous, intraperitoneal, intramuscular, intralesional, intranasal or subcutaneous administration, intrathecal administration, or instillation into a surgically created pouch or surgically placed catheter or device, or the implantation of a slow-release device e.g., a mini-osmotic pump, to the subject.

The term "enteric contrast medium" as used herein is understood to mean a dry or unsuspended component or mixture of components comprising at least one X-ray absorbing substance and optionally at least one pharmaceutically acceptable excipient, which may itself include other components, e.g., taste-masking agents, antioxidants, wetting agents, emulsifying agents, etc. The "dry suspension mixture" may subsequently be dissolved or suspended in a suspending medium to form the enteric contrast medium formulation of the invention. Terms such as "suspending medium" and "pharmaceutically acceptable excipient", as used herein, refers to the medium in which the component(s) of the enteric contrast medium are emulsified or suspended.

The terms "coating" and "coated" as herein used are understood to include coatings which are biocompatible within an environment having an acidic, or a neutral, or a basic pH value.

The terms "particle" and "particles" as used herein refers to free flowing substances of any shape which are larger than about 1 nm, such as crystals, beads (smooth, round or spherical particles), pellets, spheres, and granules. A particle may be a hollow bubble or contain multiple internal cavities. Exemplary specific sizes for the particles include from about 1 nm to about 500 microns, e.g., 1 micron to about 100 microns encompassing each single diameter value and each diameter range within the larger range across all endpoints; in various embodiments, the particles are larger than about 5 microns. Further useful particle sizes include, for example, from about 5 microns to about 100 microns, e.g., from about 20 microns to about 70 microns. A particle may contain gas or partial vacuum. A particle may be solid.

The term "suspending agent" as used herein refers to any convenient agent known in the art to be of use in forming and/or maintaining a suspension of a solid in a liquid (e.g., aqueous or oil). Exemplary suspending agents are selected from xanthan gum, guar gum, hydroxypropylmethyl cellulose, hydroxypropyl cellulose, polyvinyl pyrrolidone, alginates, and sodium carboxylmethylcellulose with xantham gum being preferred. Suspending agents may be employed in any useful amount. Exemplary useful amounts are within the range from about 0 to about 20% by weight of the powder formulation, and from about 0 to about 10% by weight of the oral suspension.

"Stable" in the context of the invention refers to suspensions that do not significantly separate into their components as different phases or layers between manufacture of the suspension and its administration to a subject in an imaging study.

The term "encapsulated gas or partial vacuum" as used herein refers to gas or vacuum that is confined and highly restricted from communication with the external environment such that a minimal amount of the gas or vacuum is released from the confined space during the expected residence time of biological use. The encapsulated gas may be at a lower, same, or higher pressure than the surrounding atmosphere or suspending liquid vehicle.

The term "high x-ray attenuation" as used herein refers to material that produces higher CT number than water and non-fat soft tissue at single energy spectrum CT imaging.

The term "low x-ray attenuation" as used herein refers to material that produces lower CT number than water and non-fat soft tissue at single energy spectrum CT imaging.

"An unpleasant and/or bitter taste" as used herein means that a majority of human patients judges said enteric contrast medium comprised as having an unpleasant and/or bitter and/or extremely bitter taste after ingestion.

With reference to the ability of the shell material of the particles in the contrast medium of the invention to affect CT number, the term "substantially" refers to the following. Exemplary shell materials contribute substantially to the CT number of the contrast medium and/or the body cavity in which the contrast medium resides at the time the CT image is acquired. "Substantially" contributes refers to the addition of at least about 30 HU to the CT number of the contrast medium and/or the body cavity in which the contrast medium resides at the time the CT image is acquired. In various embodiments, the shell material contributes at least about 50 HU, at least about 100 HU, at least about 150 HU, or at least about 200 HU to the CT number. In an exemplary embodiment, the shell material contributes more to the CT number than an equal amount of an organic polymer at the same density would contribute under the same imaging conditions. In various embodiments, the shell material contributes at least about 10% more, at least about 25% more, at least about 50% more, at least about 75% more or at least about 100% more HU units to the CT number than an equal amount of an organic polymer at the same density would contribute under the same imaging conditions.

Current clinical CT scanners can generate different X-ray spectra for imaging. The energy spectra depends mainly on the scanner tube potential (kVp) setting of the machine, which typically range from 80 to 140 kVp, and the X-ray filter which may be made of different metals (e.g. tin, aluminum, copper, gold, etc). These kVp settings result in CT scanners generating X-rays with a spectrum of energies, with the highest energy X-rays being 80 keV at a tube potential setting of 80 kVp, and 140 keV at 140 kVp. For any given monoenergetic X-ray energy passing through a known material, the extent of X-ray attenuation is defined by the Beer-Lambert law, and is proportional to a) the density of the atoms, b) the distance through the material which the X-ray passes, and c) the X-ray attenuation coefficient for that particular atom or material at that particular X-ray energy. Since the X-ray spectrum is relatively constant at any given kVp setting for a given scanner, the ratio of X-ray attenuation at 80 versus 140 kVp, as measured by Hounsfield Units (HU), can be determined for any given material. Generally, iodine and barium have an 80:140 kVp CT number ratio of about 1.7 to 1.8. Water has, by definition, an 80:140 kVp CT number ratio of 1.0 since water is defined as having 0 HU for any given X-ray spectrum at CT. The elements of the periodic table have 80:140 kVp CT number ratios that range from about 0.9 to 1.8. Materials with more widely divergent 80:140 kVp CT number ratios are more readily distinguished at dual energy or spectral CT. Other methods for obtaining dual energy CT include the selection of different tube potential settings (e.g. 70, 100, and 120 kVp) and give similar results as for 80 and 140 kVp dual energy CT. Alternative methods for obtaining dual or multi energy CT are that the x-ray spectra may be modified to obtain greater separation of the energy spectra (e.g. by application of a tin or gold filter to one of the kVp setting tubes) or other methods may be utilized to quantify the amount of absorption of different energy X-rays (e.g. sandwich detectors whereby the upper layer(s) of X-ray detectors and filters detect and block the low energy X-rays, thereby modulating the X-ray spectrum to which the lower layer(s) are exposed; photon counting detectors where detected X-rays are classified according to energy). These other methods still are of limited use to differentiate iodinated from barium-based materials, and can better differentiate materials with atoms of much different atomic number.

Virtual monoenergetic CT images are image reconstructions obtained from dual energy or spectral CT data whereby the X-ray absorption of individual voxels of the image at the given monoenergetic X-ray energy are estimates. One method to achieve virtual monoenergetic CT images is to assume that the imaged object is composed entirely of two materials, such as iodine and water, and perform a two material decomposition based on the the dual energy or spectral CT data to determine the relative x-ray attenuation attributable to iodine and water to each voxel of the image. The virtual monoenergetic CT image can then be back-extrapolated for any monoenergetic x-ray energy by using the corresponding reference x-ray attenuation coefficients for iodine and water, such as may be found on the National Institutes of Standards and Technology, to determine the CT number at the corresponding x-ray energy for each voxel of the image. By this manner, virtual monoenergetic images are obtained for a wide range of keVs, such as 40 keV or 140 keV or any energy in between or above or below these thresholds. Virtual monoenergetic images can be filtered to decrease noise and improve image quality. Virtual monoenergetic images can also be obtained by multimaterial decomposition or photon counting methods.

III. Exemplary Embodiments

A. Compositions

In various embodiments, the present invention provides enteric or non-vascular contrast agents that can be readily differentiated at CT imaging from tissues of the body and from the the available CT contrast materials on the market or that have been described in the past. By use of encapsulated gas or partial vacuum particles, with or without high x-ray attenuating materials such as iodine or barium, contrast agents can be created that have a markedly different relative CT number signal than bodily tissues or conventional iodinated and barium CT contrast materials. As an example, gas or vacuum can be encapsulated by any biocompatible material, including organic and inorganic polymers, and glasses. Exemplary materials include silicon-based material (e.g., Sift, e.g., glass), ceramic, plastic, or other shell material. In various embodiments, the encapsulating material is of use to modulate the X-ray attenuation of the overall particle and thereby create new contrast material formulations with useful X-ray attenuation properties. As an example, such encapsulated gas or partial vacuum particle contrast materials can be readily distinguished from conventional iodinated and barium CT contrast materials as well as from soft tissue and water at conventional CT. Use of dual energy or spectral CT allows even further differentiation of these contrast agents from commercial iodinated and barium contrast agents and from fat, soft tissue, and water. For example, at high-energy virtual monoenergetic CT images, such as 120 keV, the materials may show negative contrast signal, and at low energy virtual monoenergetic CT images such as 40 keV the materials may show neutral or positive contrast signal. The agents of the present invention allow for the development of a new class of contrast materials with adjustable CT number and low to high kVp CT number ratios that can be separated from each other as well as existing contrast agents and naturally occurring body tissues.

In various embodiments, the shell of the particles of the contrast media of the invention are formed from inorganic materials, e.g., silica, alumina, ceramics. Exemplary particle shells include more incorganic atoms than organic atoms by weight. Exemplary particle shells are formed from a material other than an organic polymer. Exemplary particles are not formed from polymers or copolymers prepared from acrylic acid, methacrylic acid, ethyleneimine, crotonic acid, acrylamide, ethyl acrylate, methyl methacrylate, 2-hydroxyethyl methacrylate (HEMA), lactic acid, glycolic acid, ε-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-aminobenzylstyrene, sodium styrene sulfonate, sodium 2-sulfoxyethylmethacrylate, vinyl pyridine, aminoethyl methacrylates, 2-methacryloyloxy-trimethylammonium chloride, and polyvinylidene. In various embodiments, the shell of the particles of the invention are formed from materials other than polyfunctional crosslinking monomers such as N,N'-methylenebisacrylamide, ethylene glycol dimethacrylates, 2,2'-(p-phenylenedioxy)diethyl dimethacrylate, divinylbenzene, triallylamine and methylenebis-(4-phenyl-isocyanate), or combinations thereof. Exemplary shells of the particles of the invention include materials other than polyacrylic acid, polyethyleneimine, polymethacrylic acid, polymethylmethacrylate, polysiloxane, polydimethylsiloxane, polylactic acid, polyε-caprolactone), epoxy resin, poly(ethylene oxide), poly(ethylene glycol), and polyamide (nylon). Further exemplary particle shells of the particles of the invention include materials other than copolymers include the following: polyvinylidene-polyacrylonitrile, polyvinylidene-polyacrylonitrile-polymethylmethacrylate, and polystyrene-polyacrylonitrile. In an exemplary embodiment, the shells of the particles of the contrast medium of the invention if formed of a material other than the copolymer polyvinylidene-polyacrylonitrile.

In various embodiments, the specific gravity of the particles is greater than about 0.05 g/cm$^3$. In various embodiments, the specific density of the particles of the contrast medium of the invention is at least about 0.1, at least about 0.3, at least about 0.5, at least about 0.7, at least about 1, at least about 1.5 or at least about 2 g/cm$^3$. In various embodiments, the specific gravity of the particles of the contrast medium of the invention is at least that of water.

Exemplary particles of the invention are at least partially evacuated. In various embodiments, the interior space of the particle has a pressure of less than or equal to about 1 atmosphere, e.g., less than about 0.8 atm, less than about 0.6, atm, less than about 0.3 atm or less than about 0.1 atm.

In various embodiments, the interior space of the particle is at least partially gas filled as discussed herein. When the interior of the particle is at least partially filled with a gas other than air, the gas is preferably not a hydrocarbon, fluorocarbon or a hydrofluorocarbon. In various embodiments, the gas is an elemental gas. In various embodiments, the gas is other than carbon dioxide, oxygen, nitrogen, xenon, argon, neon, helium, air or a combination thereof.

Exemplary particles of the invention are not considered "low density" particles. By low density, it is meant that the particles of the medium of the invention have an internal void (cavity) volume which is at least about 75% of the total volume of the particles. Low density also refers to particles having a void volume of at least about 80%, e.g., at least about 85%, e.g., at least about 90%, of the total volume of the particles. Exemplary particles in the medium of the invention include a void volume which is less than 75%, e.g., less than 70%, less than 65%, less than 60%, less than 50%, or less than about 30% of the total volume of the particles.

In operation, the particles of the contrast medium of the invention have distinctive properties compared to other particulate contrast media. For example, various particles of the instant contrast medium do not decrease the density of the contents of the lumen of the gastrointestinal tract or other body cavities, because the particles in general have a higher specific gravity than the contents of the lumen of the gastrointestinal tract or other body cavity. In various examples, the particles of the medium increase the density of the contents of the lumen of the intestinal tract or other body cavity.

Exemplary contrast media of the invention do not decrease the CT number of the lumen of the gastrointestinal tract or other body cavity, or do not significantly decrease the CT number in a CT image. Exemplary particles of the contrast medium do not decrease the CT number of the lumen to at least about −30 HU. Exemplary particles do not provide a decrease in HU to between about −30 HU and about −150 HU is sufficient to mark the inside of the bowel or other body cavity.

Exemplary enteric contrast media of the invention decrease the CT number by substantially less than 100 HU per 10% volume of the enteric contrast media formulation in a volume of aqueous suspension, such that to achieve a CT number of −100 HU, at least 12.5% or more of the total volume of the formulation needs to be the enteric contrast media, and to achieve a CT number of −200 HU, at least 25% or more of the total volume of the formulation needs to be the enteric contrast media. In other embodiments of the invention, the enteric contrast media of the invention may also increase the CT number of the enteric contrast media formulation.

The contrast agents of our invention can provide improved CT applications with one or more of the following benefits:
1) bowel lumen or non-vascular structures that are opacified by contrast material of the invention can be more easily differentiated from soft tissue than if opacified by currently available CT contrast material.
2) bowel or non-vascular structures can be opacified by contrast materials of the invention and be distinguished at CT imaging from vascular structures or soft tissue opacified by currently available CT contrast material;
3) enteric or nonvascular structures can be opacified with contrast of the invention for CT imaging without interfering with the assessment of intravascular contrast material related mural enhancement of those structures (bowel wall, bladder wall, other walls, including associated disease such as inflammation or neoplasms) based on CT signal at single energy spectrum CT or by relative low to high energy X-ray attenuation ratio at dual energy or spectral CT.

In various embodiments, the invention provides enteric contrast agents based on encapsulated gas or partial vacuum particles. In various embodiments, the contrast agent can be selected to give negative, neutral, or positive signal at single energy spectrum CT. In various embodiments, the contrast agent can be selected to have a very high CT number ratio from low to high kVp imaging, such as an 80:140 kVp CT number ratio of greater than about 2.1, and may be even higher than about 2.7; or from about 1.25 to about 1.5; or less than about 0.6; or less than 0.0, depending on the relative number and types other different atoms incorporated into the particle or suspending medium. In various embodiments, the contrast agent formulation include iodinated or barium materials to modulate the CT number for use with single energy spectrum CT and to modulate the 80:140 kVp CT number ratio for use with dual energy or spectral CT.

The benefits of the agents of the invention are a result of the novel X-ray imaging properties of the agents. In a CT scan, conventional positive CT contrast materials all produce similar signal—they all cause increased X-ray attenuation (positive contrast) when present and cannot be distinguished except by context. Using dual-energy or spectral CT, materials of our invention are readily differentiated from other positive contrast agents because they have markedly different relative low to high energy X-ray attenuation ratios at dual energy or spectral CT. For example, iodinated or barium-based CT contrast agents have an 80:140 kVp CT number ratio of from about 1.7 to about 1.8. In a computer simulation, elements of the periodic table were shown to have 80:140 kVp CT number ratios from about 0.9 to about 1.8. Notably, the 80:140 kVp CT number ratio of water is by definition 1.0. In the simulations, iodine- and barium-based materials had the highest theoretical 80:140 kVp CT number ratios of all the elements on the periodic table. It was not predicted that a material could have a substantially higher 80:140 kVp CT number ratio than iodine and barium, nor could an agent have a substantially lower 80:140 kVp CT number ratio than that of water. FIG. 1.

Thus, it is indeed surprising that in vitro experiments showed that materials could exist or be created that have substantially lower 80:140 kVp CT number ratios than about 0.9, or higher than about 1.8. The concentrations of two contrast materials with markedly different CT number ratios from low to high X-ray energy spectra are much more accurately quantified at dual energy CT compared with contrast materials with low to high X-ray energy spectra CT number ratios that are more similar to each other when in mixed solution. For example, the concentrations of iodine- and barium-based agents could not be quantified with much accuracy. The present invention of composite low and high X-ray attenuation material particles provide by far the largest difference in 80:140 kVp CT number ratios compared to soft tissue, water, and iodinated/barium contrast material of any compounds previously described in the literature, including in our prior patent applications. In other words, these agents are more readily distinguishable from other contrast agents and from soft tissue than any other experimental or conventionally available agent. Members of microparticles or microspheres, with or without biocompatible shell or coating, are known to be of minimal and acceptable toxicity for use as enteric contrast material.

Thus, in an exemplary embodiment, the invention provides an enteric contrast medium formulation which is formulated for enteric delivery to a subject contemporaneous with a medical imaging procedure performed on the abdomen of the subject. An exemplary formulation includes an enteric contrast medium comprising a suspension of at least one encapsulated gas or partial vacuum particle, an aqueous or oil-based component, and a suspending agent. The suspending agent maintains the at least one encapsulated gas or partial vacuum particle in an aqueous or oil suspension as a pharmaceutically acceptable enteric contrast material. Another exemplary formulation includes an enteric contrast medium comprising at least one encapsulated gas or partial vacuum particle that incorporates radiodense material such as iodine, barium, tungsten, tantalum, bismuth, or ytterbium within the particle or in the aqueous or oil suspending medium.

In an exemplary embodiment, the invention provides an enteric contrast medium, and a formulation thereof readily differentiated from other currently available contrast materials at single energy spectrum CT imaging and at dual energy or spectral CT imaging. The invention is illustrated by reference to an enteric contrast medium formulation. An exemplary formulation includes an enteric contrast medium comprising a suspension of at least one encapsulated gas or partial vacuum particle, an aqueous or oil component, and a suspending agent. The suspending agent maintains the at least one encapsulated gas or partial vacuum particle in an aqueous or oil suspension with the aqueous or oil component which is a pharmaceutically acceptable aqueous or oil vehicle. In various embodiments, the particles are coated with a material compatible with enteric administration of the formulation to a subject in need of such administration.

Exemplary encapsulating materials of the encapsulated gas or partial vacuum particle of the invention may be a glass, gel, resin, ceramic, metal, or rubber, or a plurality of these materials.

In an exemplary embodiment, the encapsulating material for the gas or partial vacuum of the particle is a glass. Exemplary glasses of use in the invention are those containing silicon dioxide, e.g., silicon dioxide blended with additives such as potash (potassium oxide), soda (sodium carbonate or sodium oxide), sodium oxide, lime (calcium oxide), boron trioxide, boric acid, magnesia, alumina, iron oxide, or other oxides. In an exemplary embodiment, the glass shell of the hollow microspheres contain silicon oxide as the sole or main component, and other chemical ingredients (mainly oxides) in the glass mentioned above are in minor quantities for the purpose of improved melting, processing and property modifications, as found in the current art of glass industry. In an exemplary embodiment, a shell of borosilicate glass consists of about 80% silica, about 13% boric oxide, about 4% sodium oxide and about 2-3% aluminum oxide.

In various embodiments, the particle is formed of a shell material defining an internal void. Exemplary shell materials contribute at least about 30 HU to the CT number of the contrast medium and/or the body cavity in which the contrast medium resides at the time the CT image is acquired. In various embodiments, the shell material contributes at least about 50 HU, at least about 100 HU, at least about 150 HU, or at least about 200 HU to the CT number. In an exemplary embodiment, the shell material contributes more to the CT number than an equal amount of an organic polymer at the same density would contribute under the same imaging conditions. In various embodiments, the shell material contributes at least about 10% more, at least about 25% more, at least about 50% more, at least about 75% more or at least about 100% more HU units to the CT number than an equal amount of an organic polymer at the same density would contribute under the same imaging conditions.

In an exemplary embodiment, the specific gravity of a glass microparticle is 0.45 g/mL. Since the specific gravity of glass is approximately 2.3 g/mL, then approximately 20% of the volume of the microparticle is glass 80% is gas/partial vacuum. When this exemplary particulate material is formulated at 20% weight/weight in formulation, the encapsulated gas or partial vacuum microparticle makes up approximately 35% of the volume of the formulation, where the gas and partial vacuum portion makes up 28% of the volume of the formulation and glass makes up 7% of the volume of the formulation. At CT imaging, gas and partial vacuum is −1000 HU at all kVp's, solid glass is about 1241 HU at 80 kVp and 1041 HU at 140 kVp, and water is 0 HU at all kVp's by definition. Therefore in this exemplary formulation the gas and partial vacuum portion contributes 28%× (−1000 HU at all kVp's)=−280 HU, the water contributes 0 HU (by definition), and the glass contributes or 7%×(1332 HU at 80 kVp)=93 HU and 7%×(1031 HU at 140 kVp)=72 HU, for an overall CT number of the formulation of −187 HU at 80 kVp and −208 HU at 140 kVp. In an actual example of physical reduction to practice, a 20% weight/weight formulation of 0.45 g/mL borosilicate glass hollow microspheres in water showed −103 HU at 80 kVp and −151 HU at 140 kVp. The slight discrepancy of HU values were likely due to the difference in composition of the actual borosilicate glass used in the hollow microspheres of the example compared to the glass used in the calculation.

In an exemplary embodiment, the encapsulated gas of the particle is a sulfur-containing gas or oxygen or carbon dioxide. In various embodiments, the gas is sulfur dioxide or sulfite.

In an exemplary embodiment, the encapsulated partial vacuum of the particle is between 0.01 and 1.0 atmospheres.

In an exemplary embodiment, the pressure of gas inside the particle is equivalent or greater than that of the atmosphere and there is no partial vacuum.

In an exemplary embodiment, the encapsulated gas or partial vacuum particle has a mean specific gravity of from about 0.2 to about 1.6 g/cc. In an exemplary embodiment, the encapsulated gas or partial vacuum particle has a mean specific gravity of between 0.1 and 1.0 g/cc. In an exemplary embodiment, the encapsulated gas or partial vacuum particle has a mean specific gravity of from about 0.3 to about 0.6 g/cc.

Exemplary encapsulated gas or partial vacuum particles of use in the formulations of the invention include borosilicate microspheres having a specific gravity similar to that of water (e.g., from about 0.3 to about 1.5 g/cc). Preferred specific gravities are from about 0.4 to about 1.4 g/cc.

One or two or more encapsulated gas or partial vacuum particle may be used together.

Any useful suspending agent or combination of suspending agents can be utilized in the formulations of the invention. In various embodiments, the suspending agent is thixotropic and forms a gel-like medium at rest but a liquid with agitation.

In an exemplary embodiment, the enteric contrast medium is formulated into a pharmaceutically acceptable carrier in which the encapsulated gas or partial vacuum particle is suspended.

In various embodiments, the encapsulating material contains a highly radiodense material, such as barium or iodine. In various embodiments, the encapsulating material contains a heavy atomic number element, such as tungsten, tantalum, ytterbium, gold, or bismuth.

In various embodiments, radiodense materials such as iodine, barium, tungsten, tantalum, ytterbium, gold, or bismuth is present in the contrast formulation as separate suspended particles or as dissolved material in the aqueous or oil-based vehicle.

In an exemplary embodiment, the encapsulated gas or partial vacuum particle is coated to provide useful properties for the contrast material, such as improved suspension in media, increased specific gravity, or altered X-ray attenuation when imaged with low or high X-ray energy spectra.

In an exemplary embodiment, the coating comprises an organic molecule with a molecular weight of less than about 3 kd, less than about 2 kd or less than about 1.5 kd. In an exemplary embodiment, the coating comprises an organic molecule with a molecular weight of less than about 3 kd, less than about 2 kd or less than about 1.5 kd, which is a member selected from an organic acid (or alcohol, amine) and its derivatives or analogs, an oligosaccharide and a combination thereof.

In an exemplary embodiment, the coating is a protein, e.g., albumin.

In various embodiments, the particles of the invention are coated with a biocompatible coating. Appropriate coatings are known in the art and it is within the abilities of one of skill in the art to select an appropriate coating for a particular formulation and/or application. See, for example, Yeh B M, Fu Y, Desai T, WO 2014145509 A1).

The suspended phase of formulations of the invention can include particles of any useful size. Exemplary specific sizes for the particles include from about 1 nm to about 500 microns, e.g., 1 micron to about 100 microns encompassing each single diameter value and each diameter range within the larger range across all endpoints; in various embodiments, the particles are larger than about 5 microns. Further useful particle sizes include, for example, from about 5 microns to about 100 microns, e.g., from about 20 microns to about 70 microns.

The formulations of the invention can include a single enteric contrast medium or two or more enteric contrast media. The media can be present in similar or different concentrations according to any useful measure of concentration. An exemplary embodiment includes different concentrations of one or more particles or soluble agents that each contribute substantially to the x-ray attenuation, relative to that of water, in the overall contrast formulation. Thus, in various embodiments, from about 5% (w/w, expressed as a weight percent, e.g. about 5 grams of contrast agent particle contained in about 100 grams of total contrast formulation) to 90% (w/w) of the weight of said formulation is said particles. In an exemplary embodiment, the formulation includes about 10% (w/w) to about 50% (w/w) of the particles.

In an exemplary embodiment, the invention provides a formulation comprising at least about 5%, e.g., at least about 20% of said encapsulated gas or partial vacuum particle.

The formulations of the invention include a population of encapsulated gas or partial vacuum particles of the invention suspended in a pharmaceutically acceptable vehicle. The vehicle includes any other useful component. For example, in some embodiments, the vehicle comprises an aqueous medium, and it further comprises an additive to impart a second property to the formulation, for example, retard dehydration of said formulation in the bowel, provide flavoring, stabilize the suspension, enhance flowability of the suspension, thicken the suspension, provide pH buffering and a combination thereof.

Formulations of the invention are distinct both molecularly and functionally and can be recognized by both characteristics. For example, in one embodiment, the enteric contrast medium has a CT number of −200 HU at 120 kVp CT imaging. In another exemplary embodiment, the enteric contrast medium has an 80:140 kVp CT number ratio of less than or equal to about 0.8. Formulations with exemplary useful values for this ratio include those with an 80:140 kVp CT number ratio of from about 0.1 to about 0.8, e.g., from about 0.3 to about 0.5, e.g., from about 0.5 to 0.7. Other formulations with exemplary useful values for this ratio include those with an 80:140 kVp CT number ratio from about 2.1 to 6.0, e.g. from about 2.3 to 2.7, e.g., from about 2.7 to 3.5. This quantity is readily determinable for any contrast medium of the invention by one of ordinary skill in the art.

In an exemplary embodiment, the invention provides an enteric contrast medium formulation, wherein the enteric contrast medium has an 80:140 kVp CT number ratio of greater than about 2.1. In an exemplary embodiment, the invention provides an enteric contrast medium formulation, wherein the enteric contrast medium has an 80:140 kVp CT number ratio from about 1.5 to 2.1. In an exemplary embodiment, the invention provides an enteric contrast medium formulation, wherein the enteric contrast medium has an 80:140 kVp CT number ratio of less than about 1.5.

In an exemplary embodiment, the formulation of the invention includes a second contrast medium different from the first contrast medium. The second contrast medium can be soluble or insoluble in the pharmaceutically acceptable vehicle. When the second contrast medium is a particulate agent, the second contrast medium can include different atoms in the particulate core, a different coating, be of a different diameter, etc. relative to the first contrast medium. The second contrast medium can also be one or more of an iodinated, Ba-, Gd-, Bi-, W-, Mg-, Ta-, Yb-, or other Si-based contrast medium.

In an exemplary embodiment, the second contrast medium is an iodinated contrast material (e.g. iohexol, iodixanol, diatrizoate, iopamidol)

In an exemplary embodiment, the second contrast medium is a barium-based contrast material (e.g. barium sulfate).

Within the scope of the invention are formulations designed for single dosage administration. These unit dosage formats contain a sufficient amount of the formulation of the invention to provide detectable contrast in a subject to whom they are administered. In an exemplary embodiment, the unit dosage formulation includes a container holding sufficient enteric contrast medium to enhance, in a diagnostically meaningful manner, a diagnostic image of a subject to whom the unit dosage has been administered. The container can be a vial, an infusion bag or any other appropriate vessel. The enteric contrast medium may be in the form of a preformulated liquid, a concentrate, or powder. In an exemplary embodiment, the subject weighs about 70 kg. In an exemplary embodiment the image is measured through the abdomen of the subject, the pelvis of the subject, or a combination thereof.

In various embodiments, the unit dosage formulation includes from about 800 to about 1500 mL of the contrast agent per adult human dose, which may be divided into smaller containers such as from about 300 to about 600 mL in size. In an exemplary embodiment, the enteric contrast medium formulation is a unit dosage formulation of from about 50 to about 100 mL. In an exemplary embodiment, the enteric contrast medium formulation is a unit dosage formulation of from about 100 mL to about 800 mL.

Any of the formulations described herein can be formulated and utilized for administration through any of a variety of routes. Exemplary routes of administration include oral, rectal, intravaginal, intravascular, intrathecal, intravesicular, and the like.

High concentrations of encapsulated gas or partial vacuum particle contrast materials have not been described for use with CT as a contrast material. In an exemplary embodiment, the encapsulated gas or partial vacuum particle in the formulation are highly concentrated, e.g., about 50 to 500 mg/g, e.g., about 100 to about 500 mg/g, e.g., about 150 to about 300 mg/g). In an exemplary embodiment, the particles account for from about 5% (w/w) to 90% (w/w), e.g., from about 5% (w/w) to about 60% (w/w) of the formulation.

In various embodiments, the enteric contrast medium of the invention and preferably its formulation exhibits chemical stability across a wide pH range (e.g., from about 1.5 to about 10). The stomach exposes enteric contents to low pH of 1.5 and bile and small bowel may expose enteric contents to high pH of up to 10. Physicochemical stability is a critical component of safety and helps minimize the risk of reactions or adverse events. Adverse reactions may occur if excessive dissolution or degradation of the materials were to occur in the gastrointestinal tract, or if the breakdown products are potentially toxic.

In various embodiments, the invention provides an enteric contrast medium and a formulation of a contrast medium with a $t_{1/2}$ that is sufficiently long to allow the completion of an imaging experiment with the concentration of encapsulated gas or partial vacuum particle remaining sufficiently high within the region of interest. In various embodiments, the invention provides an enteric contrast medium and a formulation having an in vivo residence time that is sufficiently short to allow essentially all of the administered encapsulated gas or partial vacuum particles to be eliminated from the body of the subject before being altered (metabolized, hydrolyzed, oxidized, etc.) by the subject's body.

In various embodiments, the small bowel enteric transit time of the formulation is less than 12 hours in normal subjects. In an exemplary embodiment, the formulation includes sorbitol, polyethylene glycol or both to accelerate enteric transit times.

In an exemplary embodiment, the invention provides an enteric contrast medium that dissolves slowly such that the majority of the administered encapsulated gas or partial vacuum particles are eliminated via the gastrointestinal tract prior to being altered by the subject's body, and a dissolved or altered portion is excreted by the urinary tract.

The pharmaceutical formulation of the present invention may optionally include excipients and other ingredients such as one or more sweeteners, flavors and/or additional taste modifiers to mask a bitter or unpleasant taste, suspending agents, glidants, antioxidants, preservatives and other conventional excipients as needed.

The suspension of the invention may optionally include one or more antioxidants, if necessary, taste modifiers, sweeteners, glidants, suspending agents, and preservatives.

As will be appreciated, the above optional ingredients may be added to the powder formulation of the invention, or to the oral suspension of the invention.

Antioxidants suitable for use herein include any convenient agents known in the art for this purpose such as sodium metabisulfite, sodium bisulfite, cysteine hydrochloride, citric acid, succinic acid, ascorbic acid, sodium ascorbate, fumaric acid, tartaric acid, maleic acid, malic acid, EDTA with sodium metabisulfite or sodium bisulfite being preferred.

Antioxidants may be employed in an amount which will protect the formulation from oxidation as will be apparent to one skilled in the art.

Sweeteners for use in the formulations of the invention may be any convenient agents known in the art for this purpose and may be selected from any compatible sweetener groups such as natural sweeteners like sucrose, fructose, dextrose, xylitol, sorbitol, or manitol, as well as artificial sweeteners such as aspartame, acesulfame K and sucrolose. Xylitol and aspartame are preferred sweeteners.

Flavors and flavor modifiers or taste modifiers can also be used to further improve the taste and can be any convenient agents known in the art for this purpose and include, but are not limited to, orange flavor, vanilla flavor, licorice flavor, orange vanilla flavor, creme de mint, cherry flavor, cherry vanilla flavor, berry mix flavor, passion fruit flavor, pear flavor, strawberry flavor, mandarin orange flavor, bubble gum flavor, tropical punch flavor, juicy compound for grape, grape flavor, artificial grape flavor, grape bubble gum flavor, tutti-frutti-flavor, citrus flavor, lemon flavor, chocolate flavor, coffee flavor, and combinations thereof.

Suspending agents can be any convenient agents known in the art for this purpose and can be selected from xanthan gum, guar gum, hydroxypropylmethyl cellulose, hydroxypropyl cellulose, polyvinyl pyrrolidone, alginates, and sodium carboxylmethylcellulose with xantham gum being preferred. Suspending agents may be employed in an amount within the range from about 0 to about 20% by weight of the powder formulation, and from about 0 to about 10% by weight of the oral suspension.

Preservatives can be any convenient agents known in the art for this purpose and can be selected from the group consisting of any compound compatible with drug actives such as methylparaben and propylparaben, benzoic acid, sodium benzoate, potassium sorbate, with methylparaben being preferred.

The invention also provides kits for use in a clinical and/or research setting. An exemplary kit includes: (a) a first vial containing the enteric contrast medium of the invention; (b) a second vial containing a suspension agent; and (c) directions for using and/or formulating the enteric contrast medium as a suspension. In various embodiments, the kit further comprises another vial containing a second contrast medium; and directions for administering and/or formulating the first and second enteric contrast medium in a clinical or research setting.

The contrast medium contained in the second vial can be soluble or insoluble in the pharmaceutically acceptable vehicle. When the second contrast medium is a particulate agent, the second contrast medium can include different atoms in the particulate core, a different coating, a different encapsulating material, contain a different gas, be of a different diameter, etc. relative to the first contrast medium. The second contrast medium can also be one or more of an iodinated, Ba-, Gd-, W-, Bi-, Yb-, Si- or Ta-based contrast medium.

B. Methods

The invention also provides methods of utilizing the formulations of the invention to acquire and enhance clinically meaningful CT images from a subject to whom the formulation of the invention is administered. Thus, in an exemplary embodiment, the invention provides a method of acquiring contrast enhanced CT projection data of a subject which are then reconstructed into CT images. The method includes, administering to the subject a diagnostically effective amount of said enteric contrast medium formulation of the invention; and acquiring the CT projection data of the subject which are then reconstructed into CT images. In various embodiments, the enteric contrast medium has an 80:140 kVp CT number ratio of less than about 0.8 in said image in a DECT imaging study. In various embodiments, the enteric contrast medium has an 80:140 kVp CT number ratio of greater than about 2.0 in said image in a DECT imaging study.

In an exemplary embodiment, the invention provides a contrast enhanced CT image of a subject through a region of the subject in which the enteric contrast medium of the invention is distributed.

The image of the invention, and those acquired by the method of the invention utilize a contrast medium of the invention. The image is taken through any section of the body of the subject. In an exemplary method, the image is through the abdomen and/or pelvis of the subject.

The invention also provides methods for post-processing the CT projection data, the CT images, or both to digitally separate the CT signal produced by an enteric contrast medium of the invention from CT signal produced by soft tissue, bodily fluid, or another contrast medium. In various embodiments, two-material decomposition, three-material decomposition, multi-material decomposition, or virtual monoenergetic images and a combination thereof is used to separate the dual energy or spectral CT signal produced by the enteric contrast material of the invention from CT signal produced by another contrast medium or bodily tissues based on relative differences in X-ray attenuation at low versus high X-ray energy spectra. In various embodiments, the intensity of signal, such as a threshold signal, is also considered in the material decomposition method to assist with separation of the CT signals produced by the contrast medium of the invention from CT signal produced by other imaged materials. In an exemplary embodiment of the invention, material decomposition image post-processing produces new CT images where the CT signal from the contrast material of the invention is highlighted or subtracted from the CT signal produced by the other contrast material or bodily tissues. In an exemplary embodiment of the invention, material decomposition image post-processing produces new CT images where the CT signal from a contrast material other than the contrast of the invention is highlighted or subtracted from the CT signal produced by the contrast material of the invention or bodily tissues.

One of the advantages of the contrast media and formulations of the invention is compatibility with the administration of one or more additional contrast agents through any desired route. In various embodiments, the method further comprises administering to the subject a second contrast medium different from the enteric contrast medium of the invention. In various embodiments, the second contrast medium is administered through a route selected from intravascular administration, enteric administration, anal administration and administration into a different bodily cavity that is natural (e.g. vagina, bladder), caused by injury (e.g., fistula, abscess, sinus tract), surgically created (e.g. neobladder, ileal pouch), or artificial (e.g. medical device such as a catheter, reservoir, tube, or pump). A plurality of contrast materials may be administered to different bodily compartments. In an exemplary embodiment, the second contrast medium is an iodine- or barium-based medium, and a third contrast medium is a tantalum-, bismuth-, ytterbium-, gadolinium-, or tungsten-based contrast medium. In an exemplary embodiment, the second or third contrast medium is an embodiment of a contrast medium of the invention.

In an exemplary embodiment, the contrast agent of the invention is used simultaneously with, and differentiated from, iodinated and barium agents or other contrast agents in development, such as those based on heavy metals such as tungsten, ytterbium, bismuth, or tantalum. One or multiple bodily compartments are injected and, in the case of more than one body compartment, interrogated simultaneously for a single DECT or multi-energy CT examination to provide timely high resolution perfectly co-registered anatomic images of each system for rapid and confident diagnosis. The method of the invention provides a means to accurately evaluate multi-organ injury from trauma, tumors, surgical complications, and inflammatory disease.

In an exemplary embodiment, the first and second contrast agents are distinguishable from each other in an image set encompassing a region in which both first and second contrast media are distributed. An exemplary second contrast medium is an iodinated contrast medium.

The second contrast medium can be soluble or insoluble in a pharmaceutically acceptable vehicle. When the second contrast medium is a particulate agent, the second contrast medium can include different atoms in the particulate core, a different coating, be of a different diameter, etc. relative to the first contrast agents. The second contrast medium can also be one or more of an iodinated, Ba-, Gd-, W-, Si-, Mg-, Yb-, Bi-, or Ta-based contrast medium.

In an exemplary embodiment, the second contrast medium is an iodine-based or barium-based medium.

In an exemplary embodiment, the second contrast medium is a silicon-based medium.

The invention provides methods in which CT diagnosis is improved through the use of an enteric contrast medium of one type (positive, neutral, or negative) that could also be converted by image post-processing to show one or more of the other types of signal (positive, neutral or negative) at CT. For example, in suspected bowel ischemia, neutral or negative enteric contrast is helpful to find either hyperenhancement or hypoenhancement of the bowel wall to detect inflammation or ischemia, respectively. In another exemplary method positive contrast allows identification of bowel perforation, abscesses, and fistulas.

Development of a safe clinical enteric CT contrast material that can be digitally manipulated to appear as a negative, neutral, or positive contrast material under the control of the interpreting physician would provide powerful diagnostic capability and remove guesswork and protocol errors as well as diagnostic errors. Reduced errors will result in faster diagnoses and a reduced need for additional workup. Physicians would no longer need to weigh the benefits and drawbacks of giving neutral or negative versus positive enteric contrast material for given clinical scenarios.

The following Examples are offered to illustrate exemplary embodiments of the invention and do not define or limit its scope.

EXAMPLES

Example 1

Encapsulated gas or partial vacuum microparticles are common, commercially available, and can be produced in many ways well known to practitioners of the art. A common range of methods utilize a "blowing agent," which is a substance that can release gas when heated to a high temperature. An example of production of encapsulated gas or partial vacuum microparticles is to heat shell material (in the form of glass or ceramic frit, powder, or solution) and blowing agent to a temperature sufficient to melt the shell material then cause gas release from the blowing agent to create hollow microparticles that are then cooled. Heating temperatures may range, for example, from 800 to 1500 degrees Celsius as needed for varying shell materials, to make different types of encapsulated gas or partial vacuum microparticles. Another process is to heat porous glass or ceramic material to slightly melt and seal the surface such that a gas or partial vacuum is retained inside the particles. Partial vacuum in the heating chamber can be utilized with the above methods to adjust the resultant fraction and physical characteristics of the resultant encapsulated gas or partial vacuum microparticles in the product. Gravity with or without updraft or downdraft can be utilized to modulate the residence time of particles in the heating zone, thereby influencing the diameter and specific gravity of the resultant encapsulated gas or partial vacuum microparticles. Further selection of microparticle subpopulations can be obtained by a number of mechanical means based on physical characteristics such as diameter or specific gravity.

Due to the safety considerations of enteric CT contrast formulations, the microparticle shell materials (silica, borosilicate, or glass etc) are chosen to be biologically safe and inert, e.g. those materials without toxic levels of elements such as lead, cadmium and the like.

Example 2

Stable suspension of encapsulated gas or partial vacuum microparticles in aqueous solution may be obtained by use of a suspension agent. For example, use of 0.2 to 0.5% xanthan gum was used to suspend 10 to 50% wt/wt iM30K (3M) encapsulated gas or partial vacuum particles in water. The resulting suspension of particles remained homogeneous at CT imaging for over 7 months. Slight increase in CT number at all kVp settings was seen of the suspensions after the initial 2 months. These slight increases in CT number did not substantially alter the ability of the formulation to be separated from water, soft tissue, or conventional iodinated or barium contrast material at dual energy CT imaging. The viscosity of the suspensions ranged from 50 to 2400 g/cm-sec.

Stable suspensions of encapsulated gas or partial vacuum microparticles in aqueous solution with dissolved iodinated iohexol or suspended barium sulfate were made using 0.2 to 0.5% xanthan gum. Suspensions included 30% wt/wt iM30K, 0.1% to 2% wt/wt iodine or 0.1% to 2% wt/wt barium. The suspensions containing iodine remained homogeneous at CT imaging for over 8 months after formulation. Slight increase in CT number at all kVp settings was seen of the suspensions after the initial 2 months. These slight increases in CT number did not substantially alter the ability of the formulation to be separated from water, soft tissue, or conventional iodinated or barium contrast material at dual energy CT imaging. The viscosity of the suspensions ranged from 50 to 1000 g/cm-sec.

In vivo imaging experiments in rabbits, rats, and mice demonstrated that encapsulated gas or partial vacuum particle contrast agent of the invention provides simultaneous positive, neutral and negative enteric contrast in a single DECT scan. FIGS. 8, 9, 18, and 19.

The present invention has been illustrated by reference to various exemplary embodiments and examples. As will be apparent to those of skill in the art other embodiments and variations of this invention may be devised by others skilled in the art without departing from the true spirit and scope of the invention. The appended claims are to be construed to include all such embodiments and equivalent variations.

The disclosures of each and every patent, patent application, and publication cited herein are hereby incorporated herein by reference in their entirety.

What is claimed is:

1. A method of acquiring contrast enhanced X-ray or computed tomography or dual energy computed tomography or spectral computed tomography or photon counting computed tomography projection data of a subject, the method comprising:
    orally administering to the subject a diagnostically effective amount of an enteric contrast medium formulation comprising a stable aqueous suspension of from 10% (wt/wt) to 50% (wt/wt) hollow borosilicate microspheres encapsulating gas or partial vacuum suspended in water containing 0.2% to 0.5% xanthan gum as a suspending agent maintaining the microspheres in suspension, the formulation having a viscosity of from 50 g/cm-sec to 2400 g/cm sec; and
    acquiring the projection data of the subject.

2. The method according to claim 1, wherein the X-ray or computed tomography or dual energy computed tomography or spectral computed tomography projection data is reconstructed into an image of the abdomen of the subject, where the computed tomography image is used to distinguish the enteric contrast medium formulation from other materials in the abdomen of the subject.

3. The method according to claim 1, wherein the X-ray or computed tomography or dual energy computed tomography or spectral computed tomography projection data are used for 2-material, 3-material, or multi-material decomposition and reconstructed into the image.

4. The method according to claim 1, wherein the method further comprises administering to the subject a second contrast medium different from the enteric contrast medium, and the second contrast medium is administered through a route selected from oral administration, intrathecal administration, intravesicular administration, enteric administration, anal administration, intracatheter administration, intradevice administration, intravascular administration, administration into a fistula, and administration into a surgically created pouch.

5. The method according to claim 4, wherein the enteric contrast medium and the second contrast medium are distinguishable from each other in the image based on x-ray attenuation (CT number) at single energy spectrum CT; or wherein the enteric contrast medium and the second contrast medium are distinguishable from each other in the image based on their CT number, relative X-ray attenuation at different X-ray spectra, or both.

6. The method according to claim 4 wherein the enteric contrast medium has CT number of less than about 50 Hounsfield Units in the image or less than about −50 Hounsfield Units in the image or greater than about 100 Hounsfield Units in the image.

7. The method according to claim 4 wherein the enteric contrast medium has an 80:140 kVp CT number ratio of greater than about 2.1 in the image or less than about 0.8 or less than zero in the image.

8. The method according to claim 4, wherein the second contrast medium is a member selected from an iodinated contrast medium, a Ba-, Gd-W-, Bi-, Mg-, Yb- and a Ta-based contrast medium and a silicon based contrast medium.

9. A method of acquiring contrast enhanced dual energy computed tomography or spectral computed tomography or photon counting computed tomography projection data of the abdomen of a subject, said the method comprising:
    orally administering to said the subject a diagnostically effective amount of an enteric contrast medium formulation comprising: of claim 8 a stable aqueous suspension of from 10% (wt/wt) to 50% (wt/wt) hollow borosilicate microspheres encapsulating gas or partial vacuum suspended in water containing 0.2 to 0.5% xanthan gum as a suspending agent maintaining the microspheres in suspension, the formulation having a viscosity of from 50 g/cm-sec to 2400 g/cm-sec; and acquiring said the projection data of said the subject's abdomen.

10. The method according to claim 9, wherein the enteric contrast agent distributes in the gastrointestinal tract of the subject and does not decrease the density of the contents of the gastrointestinal tract.

11. The method according to claim 9, wherein the enteric contrast agent in the intestinal tract of the subject has 80:140 kVp CT number ratio of 0.9 or less, or 1.8 or higher.

12. The method according to claim 9, wherein the enteric contrast agent wherein the small bowel transit time of the enteric contrast agent is less than 12 hours in a normal subject.

* * * * *